US00RE36350E

United States Patent [19]

Swedberg et al.

[11] E Patent Number: Re. 36,350

[45] Reissued Date of Patent: Oct. 26, 1999

[54] FULLY INTEGRATED MINIATURIZED PLANAR LIQUID SAMPLE HANDLING AND ANALYSIS DEVICE

[75] Inventors: Sally A. Swedberg, Los Altos, Calif.; Patrick Kaltenbach, Bischweier, Germany; Klaus E. Witt, Keltern, Germany; Fritz Bek, Waldbronn, Germany; Laurie S. Mittelstadt, Belmont, Calif.

[73] Assignee: Hewlett-Packard Company, Palo Alto, Calif.

[21] Appl. No.: 09/127,556

[22] Filed: Jul. 30, 1998

Related U.S. Patent Documents

Reissue of:

[64] Patent No.: 5,571,410
Issued: Nov. 5, 1996
Appl. No.: 08/486,024
Filed: Jun. 7, 1995

U.S. Applications:

[63] Continuation-in-part of application No. 08/326,111, Oct. 19, 1994, Pat. No. 5,500,071.

[51] Int. Cl.[6] ..... B01D 15/08

[52] U.S. Cl. ..... 210/198.2; 210/656; 204/451; 204/601; 422/69; 422/70

[58] Field of Search ..... 204/601, 602, 204/603, 604, 605, 451, 452, 453, 454, 455, 456; 210/635, 656, 659, 198.2; 422/68.1, 69, 70

[56] References Cited

U.S. PATENT DOCUMENTS

| | | | |
|---|---|---|---|
| 4,891,120 | 1/1990 | Sethi et al. | 204/299 |
| 4,908,112 | 3/1990 | Pace | 204/299 |
| 4,931,328 | 6/1990 | Swedberg | 204/601 |
| 5,006,313 | 4/1991 | Swedberg | 204/601 |
| 5,126,022 | 6/1992 | Soane et al. | 204/299 |
| 5,132,012 | 7/1992 | Miura et al. | 55/386 |
| 5,180,480 | 1/1993 | Manz | 204/644 |
| 5,194,133 | 3/1993 | Clark et al. | 204/299 |
| 5,198,091 | 3/1993 | Burolla | 204/601 |
| 5,291,226 | 3/1994 | Schantz et al. | 346/140 |
| 5,305,015 | 4/1994 | Schantz et al. | 346/140 |
| 5,376,252 | 12/1994 | Ekstrom | 210/198.2 |
| 5,500,071 | 3/1996 | Kaltenback | 210/198.2 |

OTHER PUBLICATIONS

Becker et al. (1986) "Fabrication of Microstructures with High Aspect Ratios and Great Structural Heights by Synchrotron Radiation Lithography, Galvanoforming, and Plastic Moulding (LIGA Process)" *Microelectric Engineering* 4:35–56.

Beckers et al. (1988) J. Chromatogr. 452:591–600.

Burggraf et al. (1994) "A Novel Approach to Ion Separations in Solutions: Sychronized Cyclic Capillary Electrophoresis (SCCE)" *Sensors and Actuators* B20:103–110.

Edmonds (1985) *Trends Anal. Chem.* 4:220.

(List continued on next page.)

*Primary Examiner*—Ernest G. Therkorn

[57] ABSTRACT

A miniaturized total analysis system ("$\mu$-TAS") comprising a miniaturized planar column device is described for use in liquid phase analysis. The $\mu$-TAS comprises microstructures fabricated by laser ablation in a variety of novel support substrates. The $\mu$-TAS includes associated laser-ablated features required for integrated sample analysis, such as analyte detection means and fluid communication means. $\mu$-TAS constructed according to the invention is useful in any analysis system for detecting and analyzing small and/or macromolecular solutes in the liquid phase and may employ chromatographic separation means, electrophoretic separation means, electrochromatographic separation means, or combinations thereof.

42 Claims, 14 Drawing Sheets

OTHER PUBLICATIONS

Effenhauser et al. (1993) "Glass Chips for High–Speed Capillary electrophoresis Separations with Submicrometer Plate Heights" *Anal. Chem.* 65:2637–2642.
Fan et al. (1994) "Micromachining of Capillary Electrophoresis Injectors and Separators on Glass Chips and Evaluation of Flow at Capillary Intersections" *Anal. Chem.* 66(1):177–184.
Frazier et al. (1994) "Development of Micromachined Devices Using Polyimide–Based Processes" *Sensors and Actuators.* A45:47–55.
Fillipini et al. (1991) *J. Biotechnol.* 18:153.
Garn et al. (1989) *Biotechnol. Bioeng.* 34:423.
Guibault (1983) *Anal. Chem. Symp. Ser.* 17:637.
Ghowsi et al. (1990) "Micellar Electrokinetic Capillary Chromatography theory Based on Electrochemical Parameters: Optimization for Three Modes of Operation" *Anal. Chem.* 62:2714–2721.
Harrison et al. (1993) "Micromachining a Miniaturized Capillary Electrophoresis–Based Chemical Analysis System on a Chip" *Science* 261:895–897.
Harrison et al. (1993) "Towards Miniaturized electrophoresis and Chemical Analysis Systems on Silicon; an Alternative to Chemical Sensors" *Sens. Actuators.* B10(2):107–116.
Jorgenson et al. (1983) *J. Chromtogr.* 255:335.
Knox et al. (1979) *J. Chromtogr.* 186:405.
Manz et al. (1990) "Design of an Open–Tubular Column Liquid Chromatograph Using Silicon Chip Technology" *Sensors and Actuators B (Chemical)* B1(1–6):249–255.
Manz et al. (1991) "Micromachining of Monocrystalline Silicon and Glass for Chemical Analysis Systems—A Look into Next Century's Technology or Just a Fashionable Craze?" *Trends. Anal. Chem.* 10(5); 144–149.
Manz et al. (1992) "Planar chips technology for miniaturization and integration of separation techniques into monitoring systems" *J. Chromatogr.* 593:253–258.
Manz et al. (1993) "Planar Chips Technology for Miniaturization of Separation Systems; A Developing Perspective in Chemical Monitoring" *Adv. Chrom.* 33:1–66.
Muller et al. (1991) *J.High Resolut. Chromatogr.* 14:174.
Olefirowicz et al. (1990) "Capillary Electrophoresis in 2 and 5 $\mu$m Diameter Capillaries: Application to Cytoplasmic Analysis" *Anal. Chem.* 62:1872–1876.
Second Int'l Symp. High–Perf. Capillary Electrophoresis (1990) *J. Chromatogr.* 516.
Stinshoff et al. (1985) "Clinical Chemistry" *Anal. Chem.* 57:114R–130R.
Tshulena (1988) *Phys. Scr.* T23:293.
Tsuda et al. (1978) *Anal. Chem.* 50:632.
Widmer (1983) *Trends Anal. Chem.* 2:8.
Widmer et al. (1984) *Int. J. Environ. Anal. Chem.* 18:1.
Znotkins. T. A. et al., *Laser Focus Electro Optics* pp. 54–70 (1987).

FULLY INTEGRATED MINIATURIZED PLANAR LIQUID SAMPLE HANDLING AND ANALYSIS DEVICE

Matter enclosed in heavy brackets [ ] appears in the original patent but forms no part of this reissue specification; matter printed in italics indicates the additions made by reissue.

CROSS-REFERENCE TO RELATED APPLICATION

This application is a continuation-in-part of U.S. patent application Ser. No. 08/326,111 filed Oct. 19, 1994, now U.S. Pat. No. 5,500,071, from which priority is claimed pursuant to 35 U.S.C. §120, and which disclosure is hereby incorporated by reference in its entirety.

TECHNICAL FIELD

The present invention relates generally to miniaturized planar column technology for liquid phase analysis. More particularly the invention relates to a miniaturized total analysis system ($\mu$-TAS) fabricated in novel separation support media using laser ablation techniques. The $\mu$-TAS disclosed herein finds use in the liquid phase analysis of either small and/or macromolecular solutes.

BACKGROUND

In sample analysis instrumentation, and especially in separation systems such as liquid chromatography and capillary electrophoresis systems, smaller dimensions will generally result in improved performance characteristics and at the same time result in reduced production and analysis costs. In this regard, miniaturized separation systems provide more effective system design, result in lower overhead due to decreased instrumentation sizing and additionally enable increased speed of analysis, decreased sample and solvent consumption and the possibility of increased detection efficiency.

Accordingly, several approaches towards miniaturization for liquid phase analysis have developed in the art; the conventional approach using drawn fused-silica capillary, and an evolving approach using silicon micromachining. What is currently thought of as conventional in miniaturization technology is generally any step toward reduction in size of the analysis system.

In conventional miniaturized technology the instrumentation has not been reduced in size; rather, it is the separation compartment size which has been significantly reduced. As an example, micro-column liquid chromatography ($\mu$LC) has been described wherein columns with diameters of 100–200 $\mu$m are employed as compared to prior column diameters of around 4.6 mm.

Another approach towards miniaturization has been the use of capillary electrophoresis (CE) which entails a separation technique carried out in capillaries 25–100 $\mu$m in diameter. CE has been demonstrated to be useful as a method for the separation of small solutes. J. Chromatogr. 218:209 (1981); Analytical Chemistry 53:1298 (1981). In contrast, polyacrylamide gel electrophoresis was originally carried out in tubes 1 mm in diameter. Both of the above described "conventional" miniaturization technologies ($\mu$LC and CE) represent a first significant step toward reducing the size of the chemical portion of a liquid phase analytical system. However, even though experimentation with such conventional miniaturized devices has helped to verify the advantages of miniaturization in principal, there nevertheless remain several major problems inherent in those technologies.

For example, there remains substantial detection limitations in conventional capillary electrophoresis technology. For example, in CE, optical detection is generally performed on-column by a single-pass detection technique wherein electromagnetic energy is passed through the sample, the light beam travelling normal to the capillary axis and crossing the capillary only a single time. Accordingly, in conventional CE systems, the detection path length is inherently limited by the diameter of the capillary.

Given Beer's law, which relates absorbance to the path length through the following relationship:

$$A=\epsilon*b*C$$

where:

A=the absorbance $\epsilon$=the molar absorptivity, (1/m*cm)

b=path length (cm)

C=concentration (m/1)

it can be readily understood that the absorbance (A) of a sample in a 25 $\mu$m capillary would be a factor of 400× less than it would be in a conventional 1 cm path length cell as typically used in UV/V is spectroscopy.

In light of this significant detection limitation, there have been a number of attempts employed in the prior art to extend detection path lengths, and hence the sensitivity of the analysis in CE systems. In U.S. Pat. No. 5,061,361 to Gordon, there has been described an approach entailing micro-manipulation of the capillary flow-cell to form a bubble at the point of detection. In U.S. Pat. No. 5,141,548 to Chervet, the use of the Z-shaped configuration in the capillary, with detection performed across the extended portion of the Z has been described. Yet another approach has sought to increase the detection path length by detecting along the major axis of the capillary (axial-beam detection). Xi et al., Analytical Chemistry 62:1580 (1990).

In U.S. Pat. No. 5,273,633 to Wang, a further approach to increased detection path lengths in CE has been described where a reflecting surface exterior of the capillary is provided, the subject system further including an incident window and an exit window downstream of the incident window. Under Wang, light entering the incident window passes through a section of the capillary by multiple internal reflections before passing through the exit window where it is detected, the subject multiple internal reflections yielding an effective increase in path length. While each of the aforementioned approaches has addressed the issue of extending the path length, each approach is limited in that it entails engineering the capillary after-the-fact or otherwise increasing the cost of the analysis.

A second major drawback in the current approach to miniaturization involves the chemical activity and chemical instability of silicon dioxide ($SiO_2$) substrates, such as silica, quartz or glass, which are commonly used in both CE and $\mu$LC systems. More particularly, silicon dioxide substrates are characterized as high energy surfaces and strongly adsorb many compounds, most notably bases. The use of silicon dioxide materials in separation systems is further restricted due to the chemical instability of those substrates, as the dissolution of $SiO_2$ materials increases in basic conditions (at pHs greater than 7.0).

To avoid the problems arising from the inherent chemical activity of silicon dioxide materials, prior separation systems have attempted chemical modifications to the inner silica surface of capillary walls. In general, such post-formation modifications are difficult as they require the provision of an interfacial layer to bond a desired surface treatment to the capillary surface, using, for example, silylating agents to create Si—O—Si—C bonds. Although such modifications may decrease the irreversible adsorption of solute molecules by the capillary surfaces, these systems still suffer from the chemical instability of Si—O—Si bonds at pHs above 7.0. Accordingly, chemical instability in $SiO_2$ materials remains a major problem.

However, despite the recognized shortcomings with the chemistry of $SiO_2$ substrates, those materials are still used in separation systems due to their desirable optical properties. In this regard, potential substitute materials which exhibit superior chemical properties compared to silicon dioxide materials are generally limited in that they are also highly adsorbing in the UV region, where detection is important.

In order to avoid some of the substantial limitations present in conventional $\mu$LC and CE techniques, and in order to enable even greater reduction in separation system sizes, there has been a trend towards providing planarized systems having capillary separation microstructures. In this regard, production of miniaturized separation systems involving fabrication of microstructures in silicon by micromachining or microlithographic techniques has been described. See, e.g. Fan et al., Anal. Chem. 66(1):177–184 (1994); Manz et al., Adv. Chrom. 33:1–66 (1993); Harrison et al., Sens. Actuators, B10 (2): 107–116 (1993); Manz et al., Trends Anal. Chem. 10 (5); 144–149 (1991); and Manz et al., Sensors and Actuators B (Chemical) B1 (1–6): 259–255 (1990).

State-of-the-art chemical analysis systems for use in chemical production, environmental analysis, medical diagnostics and basic laboratory analysis must be capable of complete automation. Such a total analysis system (TAS) (Fillipini et al (1991) J. Biotechnol. 18:153; Garn et al (1989) Biotechnol. Bioeng. 34:423; Tshulena (1988) Phys. Ser. T23:293; Edmonds (1985) Trends Anal. Chem. 4:220; Stinshoff et al. (1985) Anal. Chem. 57:114R; Guibault (1983) Anal. Chem Symp. Ser. 17:637; Widmer (1983) Trends Anal. Chem. 2:8) automatically performs functions ranging from introduction of sample into the system, transport of the sample through the system, sample preparation, separation, purification and detection, including data acquisition and evaluation. Miniaturized total analysis systems have been referred to as "$\mu$-TAS."

Recently, sample preparation technologies have been successfully reduced to miniaturized formats. Gas chromatography (Widner et al. (1984) Int. J. Environ. Anal. Chem. 18:1), high pressure liquid chromatography (Müller et al. (1991) J. High Resolut. Chromatogr. 14:174; Manz et al., (1990) Sensors & Actuators B1:249; Novotny et al., eds. (1985) Microcolumn Separations: Columns, Instrumentation and Ancillary Techniques (J. Chromatogr. Library, Vol. 30); Kucera, ed. (1984) Micro-Column High Performance Liquid Chromatography, Elsevier, Amsterdam; Scott, ed. (1984) Small Bore Liquid Chromatography Columns: Their Properties and Uses, Wiley, N.Y.; Jorgenson et al., (1983) J. Chromatogr. 255:335; Knox et al. (1979) J. Chromatogr. 186:405; Tsuda et al. (1978) Anal. Chem. 50:632) and capillary electrophoresis (Manz et al. (1992) J. Chromatogr. 593:253; Manz et al. Trends Anal. Chem. 10:144; Olefirowicz et al. (1990) Anal. Chem. 62:1872; Second Int'l Symp. High-Perf. Capillary Electrophoresis (1990) J. Chromatogr. 516; Ghowsi et al. (1990) Anal. Chem. 62:2714) have been reduced to miniaturized formats.

Capillary electrophoresis has been particularly amenable to miniaturization because the separation efficiency is proportional to the applied voltage regardless of the length of the capillary Harrison et al. (1993) Science 261:895–897. A capillary electrophoresis device using electroosmotic fluid pumping and laser fluorescence detection has been prepared on a planar glass microstructure. Effenhauser et al. (1993) Anal. Chem. 65:2637–2642; Burggraf et al. (1994) Sensors and Actuators B20:103–110. In contrast to silicon materials (see, Harrison et al. (1993) Sensors and Actuators B10:107–116), polyimide has a very high breakdown voltage, thereby allowing the use of significantly higher voltages.

The use of micromachining techniques to fabricate separation systems in silicon provides the practical benefit of enabling mass production of such systems. In this regard, a number of established techniques developed by the microelectronics industry involving micromachining of planar materials, such as silicon, exist and provide a useful and well accepted approach to miniaturization. Examples of the use of such micromachining techniques to produce miniaturized separation devices on silicon or borosilicate glass chips can be found in U.S. Pat. No. 5,194,133 to Clark et al.; U.S. Pat. No. 5,132,012 to Miura et al.; in U.S. Pat. No. 4,908,112 to Pace; and in U.S. Pat. No. 4,891,120 to Sethi et al.

Micromachining silicon substrates to form miniaturized separation systems generally involves a combination of film deposition, photolithography, etching and bonding techniques to fabricate a wide array of three dimensional structures. Silicon provides a useful substrate in this regard since it exhibits high strength and hardness characteristics and can be micromachined to provide structures having dimensions in the order of a few micrometers.

Although silicon micromachining has been useful in the fabrication of miniaturized systems on a single surface, there are significant disadvantages to the use of this approach in creating the analysis device portion of a miniaturized separation system.

Initially, silicon micromachining is not amenable to producing a high degree of alignment between two etched or machined pieces. This has a negative impact on the symmetry and shape of a separation channel formed by micromachining, which in turn may impact separation efficiency. Secondly, sealing of micromachined silicon surfaces is generally carried out using adhesives which may be prone to attack by separation conditions imposed by liquid phase analyses. Furthermore, under oxidizing conditions, a silica surface is formed on the silicon chip substrate. In this regard, silicon micromachining is also fundamentally limited by the chemistry of $SiO_2$. Accordingly, there has remained a need for an improved miniaturized total analysis system which is able to avoid the inherent shortcomings of conventional miniaturization and silicon micromachining techniques.

SUMMARY OF THE INVENTION

The present invention relates to a miniaturized planar column device for use in a liquid phase analysis system. It is a primary object of the present invention to provide a miniaturized column device laser-ablated in a substantially planar substrate, wherein said substrate is comprised of a material selected to avoid the inherent chemical activity and pH instability encountered with silicon and prior silicon dioxide-based device substrates.

The present invention is also related to the provision of detection means engineered into a miniaturized planar column device whereby enhanced on-column analysis or detection of components in a liquid sample is enabled. It is further contemplated to provide a column device for liquid phase analysis having detection means designed into the device in significantly compact form as compared to conventional technology. In one particular aspect of the present invention, it is contemplated to provide optical detection means ablated in a miniaturized planar column device and having a substantially enhanced detection path length.

It is a further related object of the present invention to provide a device featuring improved means for liquid handling, including sample injection, and to provide a miniaturized column device with means to interface with a variety of external liquid reservoirs. Specifically contemplated herein is a system design which allows a variety of injection methods to be readily adapted to the planar structure, such as pressure injection, hydrodynamic injection or electrokinetic injection.

It is yet a further related object of the present invention to provide a miniaturized total chemical analysis system ($\mu$-TAS) fully contained on a single, planar surface. In this regard, a miniaturized system according to the present invention is capable of performing complex sample handling, separation, and detection methods with reduced technician manipulation or interaction. Accordingly, the subject invention finds potential application in monitoring and/or analysis of components in industrial chemical, biological, biochemical and medical processes and the like.

A particular advantage of the present invention is the use of processes other than silicon micromachining techniques or etching techniques to create miniaturized columns in a wide variety of polymeric and ceramic substrates having desirable attributes for an analysis portion of a separation system. More specifically, it is contemplated herein to provide a miniaturized planar column device by ablating component microstructures in a substrate using laser radiation. In one preferred embodiment, a miniaturized column device is formed by providing two substantially planar halves having microstructures laser-ablated thereon, which, when the two halves are folded upon each other, define a sample processing compartment featuring enhanced symmetry and axial alignment.

Use of laser ablation techniques to form miniaturized devices according to the present invention affords several advantages over prior etching and micromachining techniques used to form systems in silicon or silicon dioxide materials. Initially, the capability of applying rigid computerized control over laser ablation processes allows microstructure formation to be executed with great precision, thereby enabling a heightened degree of alignment in structures formed by component parts. The laser ablation process also avoids problems encountered with microlithographic isotropic etching techniques which may undercut masking during etching, giving rise to asymmetrical structures having curved side walls and flat bottoms.

Laser ablation further enables the creation of microstructures with greatly reduced component size. In this regard, microstructures formed according to the invention are capable of having aspect ratios several orders of magnitude higher than possible using prior etching techniques, thereby providing enhanced sample processing capabilities in such devices. The use of laser-ablation processes to form microstructures in substrates such as polymers increases ease of fabrication and lowers per-unit manufacturing costs in the subject devices as compared to prior approaches such as micromachining devices in silicon. In this regard, devices formed according to the invention in low-cost polymer substrates have the added feature of being capable of use as substantially disposable miniaturized column units.

In another aspect of the instant invention, laser-ablation in planar substrates allows for the formation of microstructures of almost any geometry or shape. This feature not only enables the formation of complex device configurations, but further allows for integration of sample preparation, sample injection, post-column reaction and detection means in a miniaturized total analysis system of greatly reduced overall dimensions.

The compactness of the analysis portion in a device produced under to the present invention, in conjunction with the feature that integral functions such as injection, sample handling and detection may be specifically engineered into the subject device to provide a $\mu$-TAS device, further allows for integrated design of system hardware to achieve a greatly reduced system footprint.

By the present invention, inherent weaknesses existing in prior approaches to liquid phase separation device miniaturization, and problems in using silicon micromachining techniques to form miniaturized column devices have been addressed. Accordingly, the present invention discloses a miniaturized total analysis system capable of performing a variety of liquid phase analyses on a wide array of liquid samples.

DETAILED DESCRIPTION OF THE INVENTION

Figure 1:
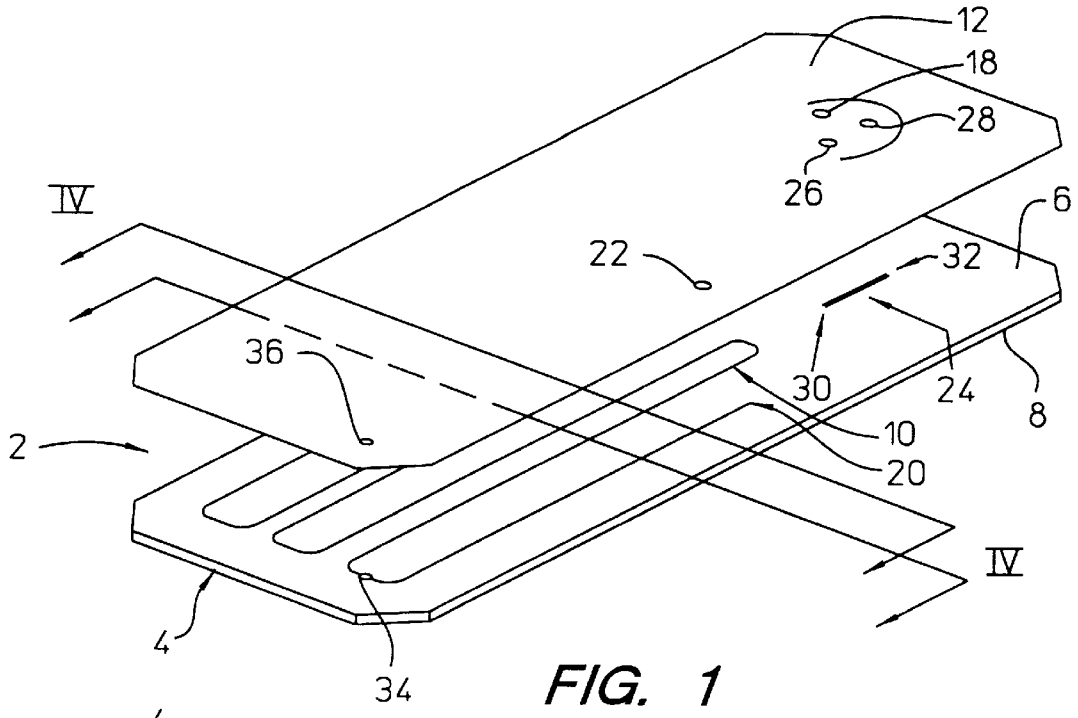
FIG. 1 is an exploded view of a miniaturized column device constructed in accordance with the present invention.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "a detection means" includes two or more such detection means, reference to "a sample flow component" includes more than one such component, reference to "an on-device fluid reservoir compartment" includes two or more such compartments, and the like.

In this specification and in the claims which follow, reference will be made to a number of terms which shall be defined to have the following meanings:

The term "substrate" is used herein to refer to any material which is UV-adsorbing, capable of being laser-ablated and which is not silicon or a silicon dioxide material such as quartz, fused silica or glass (borosilicates). Accordingly, miniaturized column devices are formed herein using suitable substrates, such as laser ablatable polymers (including polyimides and the like) and ceramics (including aluminum oxides and the like). Further, miniaturized column devices are formed herein using composite substrates such as laminates. A "laminate" refers to a composite material formed from several different bonded layers of same or different materials. One particularly preferred composite substrate comprises a polyimide laminate formed from a first layer of polyimide, such as Kapton® (DuPont; Wilmington, Del.), that has been co-extruded with a second, thin layer of a thermal adhesive form of polyimide known as KJ® (DuPont). This thermoplastic adhesive can be applied to one or both sides of the first polyimide layer, thereby providing a means for producing a laminate of desired thickness.

The term "sample handling region" refers to a portion of a microchannel, or to a portion of a "sample processing compartment" that is formed upon enclosure of the microchannel by a cover plate or substrate in which a mirror image of the microchannel has been laser ablated as described in detail below, that includes a "sample flow component" or a "sample treatment component." By the term "sample flow component" is intended a portion of the sample processing compartment that interconnects sample treatment components.

A "sample treatment component" is a portion of the sample processing compartment in which particular sample preparation chemistries are done. In particular, an analyte of interest is generally obtained in a matrix containing other species which may potentially interfere with the detection and analysis of the analyte. Accordingly, a sample treatment component is a portion of the sample processing compartment in which analyte separation from the matrix is effected. Examples of functions which may be served by the sample treatment component include chromatographic separations, electrophoretic separations, electrochromatographic separations, and the like.

As used herein, the term "detection means" refers to any means, structure or configuration which allows one to interrogate a sample within the sample processing compartment using analytical detection techniques well known in the art. Thus, a detection means includes one or more apertures, elongated apertures or grooves which communicate with the sample processing compartment and allow an external detection apparatus or device to be interfaced with the sample processing compartment to detect an analyte passing through the compartment.

Changes in the electrochemical properties of a liquid sample passing through the sample processing compartment can be detected using detection means which physically contact the sample passing through the sample processing compartment. In one embodiment, an electrode may be placed within, or butt-coupled to a detection means such as an aperture or a groove, thereby enabling the electrode to directly contact the sample stream. By arranging two dissimilar electrodes (which are connected through an external conducting circuit) opposite each other relative to the sample processing compartment, an electric field can be generated in the sample processing compartment—transverse to the direction of sample flow—thereby providing a ready means of electrochemical detection of analytes passing through the compartment.

Changes in the electrical properties of a liquid sample passing through the sample processing compartment can be detected using detection means which do not physically contact the sample passing through the sample processing compartment. Thus, "changes in the electrical properties" of a sample passing through the sample processing compartment refers to detectable changes in the conductivity, permittivity, or both of a particular sample due to the presence of an analyte in the sample. The "conductivity" of a sample refers to the ratio of the electric current density to the electric field in that sample. The "permittivity" of a sample refers to the dielectric constant of a sample multiplied by the permittivity of empty space, where the permittivity of empty space ($\epsilon_0$) is a constant appearing in Coulomn's law having the value of 1 in centimeter-gram-second electrostatic units.

Changes in the electrical properties of a sample passing through a sample processing compartment are measured herein by detection of the impedance of the liquid sample. The "impedance" or "electrical impedance" of a circuit refers to the total opposition that the circuit presents to an alternating current ("AC"), equal to the complex ratio of the voltage to the current in complex notation. Thus, the magnitude of the total opposition that a circuit presents to an alternating current is equal to the ratio of the maximum voltage in an AC circuit to the maximum current. An "electrical impedance meter" refers to an instrument which measures the complex ratio of voltage to current in a given circuit at a given frequency.

A plurality of electrical "communication paths" capable of carrying and/or transmitting electric current can be arranged adjacent to the sample processing compartment such that the communication paths, in combination, form a circuit. As used herein, a communication path includes any conductive material which is capable of transmitting or receiving an AC signal. A particularly preferred conductive material is copper. Thus, in one embodiment, a plurality of communication paths forming an antenna circuit (e.g., a pair of copper antennae) are arranged adjacent to the sample processing compartment whereby a circuit is formed capable of passing an oscillating voltage through the sample processing compartment which is sensitive to changes in the impedance of a liquid sample flowing therethrough. An "antenna" refers to a device capable of radiating and/or receiving radio waves such as alternating current (AC) signal. An "antenna circuit" intends a complete electrical circuit which includes an antenna. An "antenna coil" refers to a coil through which antenna current (e.g., an AC signal) flows.

Further, by the arrangement of two detection means opposite each other relative to the sample processing compartment, a "detection path" is conveniently formed, thereby allowing detection of analytes passing through the sample processing compartment using detection techniques well known in the art.

An "optical detection path" refers to a configuration or arrangement of detection means to form a path whereby radiation, such as a ray of light, is able to travel from an external source to a means for receiving radiation—wherein the radiation traverses the sample processing compartment and can be influenced by the sample or separated analytes in the sample flowing through the sample processing compartment. An optical detection path is generally formed according to the invention by positioning a pair of detection means directly opposite each other relative to the sample processing compartment. In this configuration, analytes passing through the sample processing compartment can be detected via transmission of radiation orthogonal to the major axis of the sample processing compartment (and, accordingly, orthogonal to the direction of electroosmotic flow in an electrophoretic separation). A variety of external optical detection techniques can be readily interfaced with the sample processing compartment using an optical detection path including, but not limited to, UV/Vis, Near IR, fluorescence, refractive index (RI) and Raman techniques.

As used herein, the term "transparent" refers to the ability of a substrate to transmit light of different wavelengths, which ability may be measured in a particular substance as the percent of radiation which penetrates a distance of 1 meter. Thus, according to the invention, a "transparent sheet" is defined as a sheet of a substance which is transmissive to specific types of radiation or particles of interest. Transparent sheets which are particularly employed in the invention in the context of optical detection configurations are formed from materials such as, but not limited to, quartz, sapphire, diamond and fused silica.

In the context of UV-visible absorption detection of sample analytes herein, the terms "path length," or "optical path length" refer to an optical path length "b" derived from Beer's law, which states that $A=\log(I_i/I_f)=\epsilon*b*C$, wherein A is the absorbance, $I_i$ is the light intensity measured in the absence of the analyte, $I_f$ is the light intensity transmitted through the analyte, $\epsilon$ is the molar extinction coefficient of the sample (1/m*cm), C is the analyte concentration (m/1), and b is the optical path length (cm). Thus, in a detection configuration wherein UV-Vis absorption of a sample analyte is measured via an optical detection path by passing light through the sample processing compartment along a path perpendicular to the sample processing compartment major axis, the path length (b) of the measurement is substantially defined by the dimensions of the sample processing compartment.

A "detection intersection" refers to a configuration wherein a plurality of detection means that communicate with the sample processing compartment converge at a particular location in the sample processing compartment. In this manner, a number of detection techniques can be simultaneously performed on a sample or separated analyte at the detection intersection. According to the invention, a detection intersection is formed when a plurality of detection paths cross, or when a detection means such as an aperture communicates with the sample processing compartment at substantially the same point as a detection path. The sample, or a separated analyte, can thus be interrogated using a combination of UV/Vis and fluorescence techniques, optical and electrochemical techniques, optical and electrical techniques, or like combinations to provide highly sensitive detection information. See, e.g., Beckers et al. (1988) J. Chromatogr. 452:591–600; and U.S. Pat. No. 4,927,265, to Brownlee.

As used herein, a "lightguide means" refers to a substantially long, thin thread of a transparent substance which can be used to transmit light. Lightguide means useful in the practice of the invention include optical fibers, integrated lens configurations and the like. In particularly preferred embodiments, optical fibers are interfaced with detection means to enable optical detection techniques known in the art. The terms "optical fiber," "fiber optic waveguide" or "optical fiber means" are used herein to refer to a single optical fiber or a bundle optical fibers, optionally encased in a protective cladding material. Examples of suitable optical fiber substrate materials include glass, plastic, glass/glass composite and glass/plastic composite fibers. A critical characteristic of optical fibers is attenuation of an optical signal. Further, a chemical sensor can be incorporated into a fiber optic waveguide in a manner such that the chemical sensor will interact with the liquid sample analyte. Structures, properties, functions and operational details of such fiber optic chemical sensors can be found in U.S. Pat. No. 4,577,109 to Hirschfeld, U.S. Pat. No. 4,785,814 to Kane, and U.S. Pat. No. 4,842,783 to Blaylock.

The use of laser ablation techniques in the practice of the invention allows for a high degree of precision in the alignment of micro-scale components and structures, which alignment has either been difficult or not possible in prior silicon or glass substrate-based devices. Thus, the term "microalignment" as used herein refers to the precise and accurate alignment of laser-ablated features, including the enhanced alignment of complementary microchannels or microcompartments with each other, inlet and/or outlet ports with microchannels or separation compartments, detection means with microchannels or separation compartments, detection means with other detection means, and the like.

The term "microalignment means" is defined herein to refer to any means for ensuring the precise microalignment of laser-ablated features in a miniaturized column device. Microalignment means can be formed in the column devices either by laser ablation or by other methods of fabricating shaped pieces well known in the art. Representative microalignment means that can be employed herein include a plurality of co-axially arranged apertures laser-ablated in component parts and/or a plurality of corresponding features in column device substrates, e.g., projections and mating depressions, grooves and mating ridges or the like. Further, the accurate microalignment of component parts can be effected by forming the miniaturized columns in flexible substrates having at least one fold means laser-ablated therein, such that sections of the substrate can be folded to overlie other sections thereby forming composite micro-scale compartments, aligning features such as apertures or detection means with separation compartments, or forming micro-scale separation compartments from microchannels. Such fold means can be embodied by a row of spaced-apart perforations ablated in a particular substrate, spaced-apart slot-like depressions or apertures ablated so as to extend only part way through the substrate, or the like. The perforations or depressions can have circular, diamond, hexagonal or other shapes that promote hinge formation along a predetermined straight line.

The term "liquid phase analysis" is used to refer to any analysis which is done on either small and/or macromolecular solutes in the liquid phase. Accordingly, "liquid phase analysis" as used herein includes chromatographic separations, electrophoretic separations, and electrochromatographic separations.

In this regard, "chromatographic" processes generally comprise preferential separations of components, and include reverse-phase, hydrophobic interaction, ion exchange, molecular sieve chromatography and like methods.

"Electrophoretic" separations refers to the migration of particles or macromolecules having a net electric charge where said migration is influenced by an electric field. Accordingly electrophoretic separations contemplated for use in the invention include separations performed in columns packed with gels (such as polyacrylamide, agarose and combinations thereof) as well as separations performed in solution.

"Electrochromatographic" separation refers to combinations of electrophoretic and chromatographic techniques. Exemplary electrochromatographic separations include packed column separations using electromotive force (Knox et al. (1987) Chromatographia 24:135; Knox et al. (1989) J. Liq. Chromatogr 12:2435; Knox et al. (1991) Chromatographia 32:317), and micellar electrophoretic separations (Terabe et al. (1985) Anal. Chem. 57:834–841).

The term "motive force" is used to refer to any means for inducing movement of a sample along a column in a liquid phase analysis, and includes application of an electric potential across any portion of the column, application of a pressure differential across any portion of the column or any combination thereof.

The term "surface treatment" is used to refer to preparation or modification of the surface of a microchannel which will be in contact with a sample during separation, whereby the separation characteristics of the device are altered or otherwise enhanced. Accordingly, "surface treatment" as used herein includes: physical surface adsorptions; covalent bonding of selected moieties to functional groups on the surface of microchannel substrates (such as to amine, hydroxyl or carboxylic acid groups on condensation polymers); methods of coating surfaces, including dynamic deactivation of channel surfaces (such as by adding surfactants to media), polymer grafting to the surface of channel substrates (such as polystyrene or divinyl-benzene) and thin-film deposition of materials such as diamond or sapphire to microchannel substrates.

The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

In general, any substrate which is UV absorbing provides a suitable substrate in which one may laser ablate features. Accordingly, under the present invention, microstructures of selected configurations can be formed by imaging a lithographic mask onto a suitable substrate, such as a polymer or ceramic material, and then laser ablating the substrate with laser light in areas that are unprotected by the lithographic mask.

In laser ablation, short pulses of intense ultraviolet light are absorbed in a thin surface layer of material within about 1 $\mu$m or less of the surface. Preferred pulse energies are greater than about 100 millijoules per square centimeter and pulse durations are shorter than about 1 microsecond. Under these conditions, the intense ultraviolet light photodissociates the chemical bonds in the material. Furthermore, the absorbed ultraviolet energy is concentrated in such a small volume of material that it rapidly heats the dissociated fragments and ejects them away from the surface of the material. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer.

Although laser ablation has been described herein using an excimer laser, it is to be understood that other ultraviolet light sources with substantially the same optical wavelength and energy density may be used to accomplish the ablation process. Preferably, the wavelength of such an ultraviolet light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques, such as those described above, have been described in the art. Znotins, T. A., et al., Laser Focus Electro Optics, (1987) pp. 54–70; U.S. Pat. Nos. 5,291,226 and 5,305,015 to Schantz et al.

The term "injection molding" is used to refer to a process for molding plastic or nonplastic ceramic shapes by injecting a measured quantity of a molten plastic or ceramic substrate into dies (or molds). In one embodiment of the present invention, miniaturized column devices may be produced using injection molding.

More particularly, it is contemplated to form a mold or die of a miniaturized column device wherein excimer laser-ablation is used to define an original microstructure pattern in a suitable polymer substrate. The microstructure thus formed may then be coated by a very thin metal layer and electroplated (such as by galvano forming) with a metal such as nickel to provide a carrier. When the metal carrier is separated from the original polymer, an mold insert (or tooling) is provided having the negative structure of the polymer. Accordingly, multiple replicas of the ablated microstructure pattern may be made in suitable polymer or ceramic substrates using injection molding techniques well known in the art.

The term "LIGA process" is used to refer to a process for fabricating microstructures having high aspect ratios and increased structural precision using synchrotron radiation lithography, galvanoforming, and plastic molding. In a LIGA process, radiation sensitive plastics are lithographically irradiated at high energy radiation using a synchrotron source to create desired microstructures (such as channels, ports, apertures and micro-alignment means), thereby forming a primary template.

The primary template is then filled with a metal by electrodeposition techniques. The metal structure thus formed comprises a mold insert for the fabrication of secondary plastic templates which take the place of the primary template. In this manner highly accurate replicas of the original microstructures may be formed in a variety of substrates using injection or reactive injection molding techniques. The LIGA process has been described by Becker, E. W., et al., Microelectric Engineering (1986) 4:35–56. Descriptions of numerous polymer substrates which may be injection molded using LIGA templates, and which are suitable substrates in the practice of the subject invention, may be found in "Contemporary Polymer Chemistry", Allcock. H. R. and Lampe, F. W. (Prentice-Hall, Inc.) New Jersey (1981).

"Optional" or "optionally" means that the subsequently described feature or structure may or may not be present in the $\mu$-TAS or that the subsequently described event or circumstance may or may not occur, and that the description includes instances where said feature or structure is present and instances where the feature or structure is absent, or instances where the event or circumstance occurs and instances where it does not. For example, the phrase "a $\mu$-TAS optionally having detection means" intends that access ports may or may not be present on the device and that the description includes both circumstances where access ports are present and absent.

Accordingly, the invention concerns formation of miniaturized column devices including $\mu$-TAS, using laser ablation in a suitable substrate. It is also contemplated to form column devices and $\mu$-TASs according to the invention using injection molding techniques wherein the original microstructure has been formed by an excimer laser ablation process, or where the original microstructure has been formed using a LIGA process.

More particularly, microstructures such as sample processing compartments, injection means, detection means and micro-alignment means may be formed in a planar substrate by excimer laser ablation. A frequency multiplied YAG laser may also be used in place of the excimer laser. In such a case, a complex microstructure pattern useful for practicing the invention may be formed on a suitable polymeric or ceramic substrate by combining a masking process with a laser ablation means, such as in a step-and-repeat process, where such processes would be readily understood by one of ordinary skill in the art.

In the practice of the invention, a preferred substrate comprises a polyimide material such as those available under the trademarks Kapton® or Upilex® from DuPont (Wilmington, Del.), although the particular substrate selected may comprise any other suitable polymer or ceramic substrate. Polymer materials particularly contemplated herein include materials selected from the following classes: polyimide, polycarbonate, polyester, polyamide, polyether, polyolefin, or mixtures thereof. Further, the polymer material selected may be produced in long strips on a reel, and, optional sprocket holes along the sides of the material may be provided to accurately and securely transport the substrate through a step-and-repeat process.

According to the invention, the selected polymer material is transported to a laser processing chamber and laser-ablated in a pattern defined by one or more masks using laser radiation. In a preferred embodiment, such masks define all of the ablated features for an extended area of the material, for example encompassing multiple apertures (including inlet and outlet ports), micro-alignment means and sample processing chambers.

Alternatively, patterns such as the aperture pattern, the sample processing channel pattern, etc., may be placed side by side on a common mask substrate which is substantially larger than the laser beam. Such patterns may then be moved sequentially into the beam. In other contemplated production methods, one or more masks may be used to form apertures through the substrate, and another mask and laser energy level (and/or number of laser shots) may be used to define sample processing channels which are only formed through a portion of the thickness of the substrate. The masking material used in such masks will preferably be highly reflecting at the laser wavelength, consisting of, for example, a multilayer dielectric material or a metal such as aluminum.

The laser ablation system employed in the invention generally includes beam delivery optics, alignment optics, a high precision and high speed mask shuttle system, and a processing chamber including mechanism for handling and positioning the material. In a preferred embodiment, the laser system uses a projection mask configuration wherein a precision lens interposed between the mask and the substrate projects the excimer laser light onto the substrate in the image of the pattern defined on the mask.

It will be readily apparent to one of ordinary skill in the art that laser ablation may be used to form miniaturized sample processing channels and apertures in a wide variety of geometries. Any geometry which does not include undercutting may be provided using ablation techniques, such as modulation of laser light intensity across the substrate, stepping the beam across the surface or stepping the fluence and number of pulses applied to each location to control corresponding depth. Further, laser-ablated channels or chambers produced according to the invention are easily fabricated having ratios of channel depth to channel width which are much greater than previously possible using etching techniques such as silicon micromachining. Such aspect ratios can easily exceed unity, and may even reach to 10. Furthermore, the aspect ratio of laser-ablated channels and chambers can be less than one, i.e., the width of the channel or chamber can be greater than the depth.

In a preferred embodiment of the invention, channels of a semi-circular cross section are laser ablated by controlling exposure intensity or by making multiple exposures with the beam being reoriented between each exposure. Accordingly, when a corresponding semi-circular channel is aligned with a channel thus formed, a sample processing chamber of highly symmetrical circular cross-section is defined which may be desirable for enhanced fluid flow through the sample processing device.

As a final step in laser ablation processes contemplated by the invention, a cleaning step is performed wherein the laser-ablated portion of the substrate is positioned under a cleaning station. At the cleaning station, debris from the laser ablation are removed according to standard industry practice.

As will be appreciated by those working in the field of liquid phase analysis devices, the above-described method may be used to produce a wide variety of miniaturized devices. One such device is represented in FIG. 1 where a particular embodiment of a miniaturized column device is generally indicated at 2. Generally, miniaturized column 2 is formed in a selected substrate 4 using laser ablation techniques. The substrate 4 generally comprises first and second substantially planar opposing surfaces indicated at 6 and 8 respectively, and is selected from a material other than silicon which is UV absorbing and, accordingly, laser-ablatable.

In a particular embodiment of the invention, the miniaturized column device 2 comprises a column structure ablated on a chip, which, in the practice of the invention may be a machinable form of the plastic polyimide such as Vespel®. It is particularly contemplated in the invention to use such a polyimide substrate as, based on considerable experience with the shortcomings of fused silica and research into alternatives thereof, polyimides have proved to be a highly desirable substrate material for the analysis portion of a liquid phase sample processing system.

In this regard, it has been demonstrated that polyimides exhibit low sorptive properties towards proteins, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface which may provide a variety of desirable surface properties, depending on the target analysis. Unlike prior silicon dioxide based systems, these bonds to the polymeric substrate demonstrate pH stability in the basic region (pH 9–10).

Figure 2:
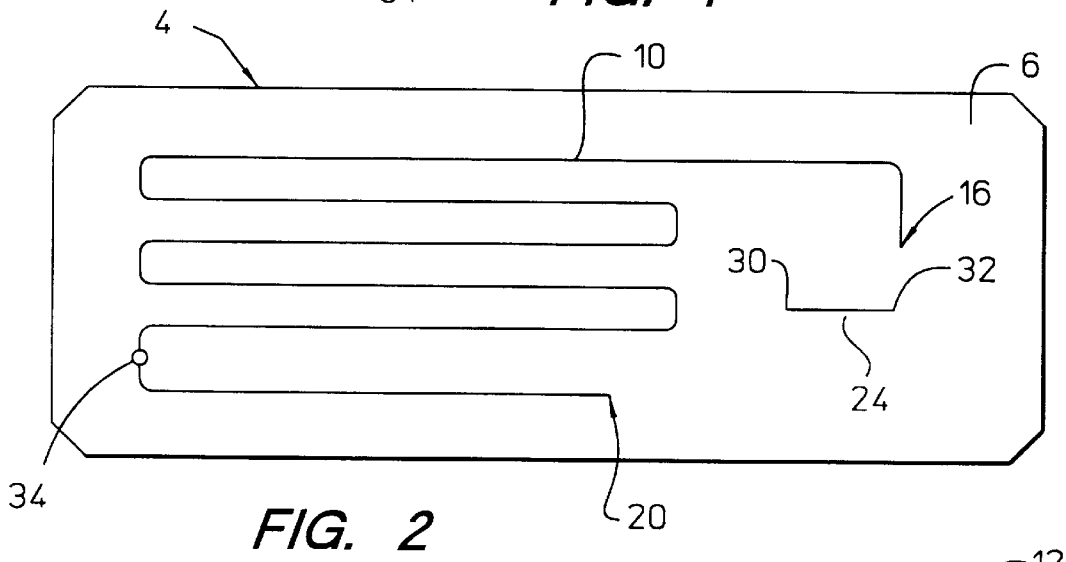
FIG. 2 is a plan view of the interior surface of the miniaturized column device of FIG. 1.
Figure 3:
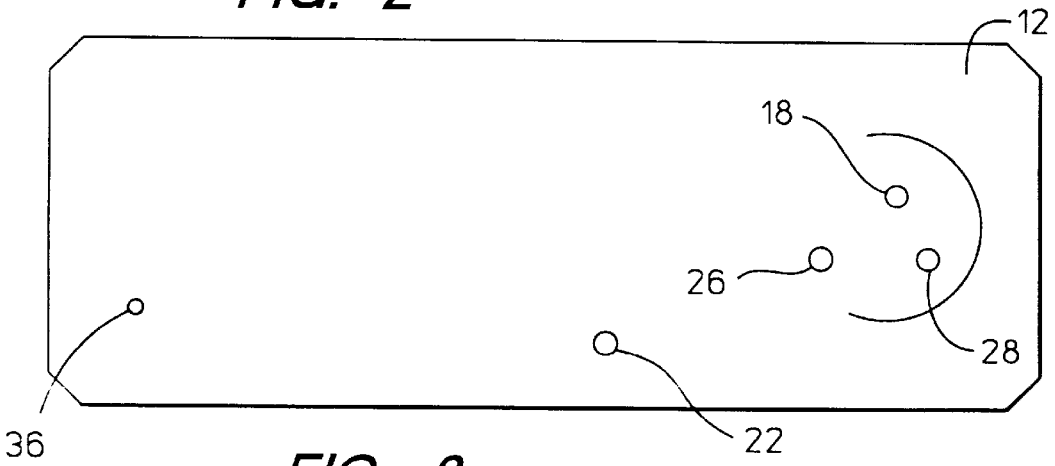
FIG. 3 is a plan view of the exterior surface of the device of FIG. 1.

Referring now to FIGS. 1–3, the substrate 4 has a microchannel 10 laser-ablated in a first planar surface 6. It will be readily appreciated that, although the microchannel 10 has been represented in a generally extended form, microchannels formed according to the invention may be ablated in a large variety of configurations, such as in a straight, serpentine, spiral, or any tortuous path desired. Further, as described in greater detail above, the microchannel 10 may be formed in a wide variety of channel geometries including semi-circular, rectangular, rhomboid, and the like, and the channels may be formed in a wide range of aspect ratios. It is also noted that a device having a plurality of microchannels laser-ablated thereon falls within the spirit of the present invention.

Figure 4:
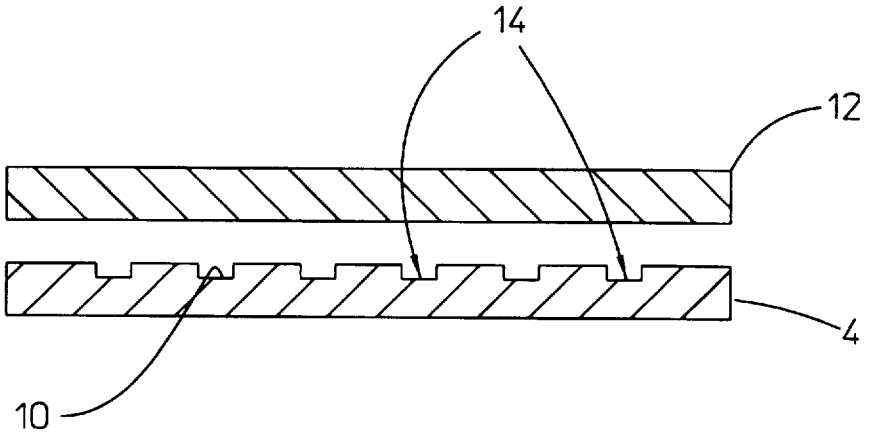
FIG. 4 is a cross-sectional side view of the miniaturized column device of FIG. 1, taken along lines IV—IV and showing formation of a sample processing compartment according to the invention.

Referring particularly to FIGS. 1 and 4, a cover plate 12 is arranged over said first planar surface 6 and, in combination with the laser-ablated microchannel 10, forms an elongate sample processing compartment 14. Cover plate 12 may be formed from any suitable substrate such as polyimide, the selection of the substrate only being limited by avoidance of undesirable separation surfaces such as silicon or silicon dioxide materials.

According to the invention, cover plate 12 may be fixably aligned over the first planar surface 6 to form a liquid-tight sample processing compartment by using pressure sealing techniques, by using external means to urge the pieces together (such as clips, tension springs or associated clamping apparatus) or by using adhesives well known in the art of bonding polymers, ceramics and the like.

Referring to FIGS. 1–4, a particular embodiment of the invention is shown wherein cover plate 12 further comprises apertures ablated therein. In this regard, a first aperture communicates with the sample processing compartment 14 at a first end 16 thereof to form an inlet port 18 enabling the passage of fluid from an external source into said sample processing compartment. A second aperture communicates with the sample processing compartment 14 at a second end 20 thereof to form an outlet port 22 enabling passage of fluid from the sample processing compartment to an external receptacle. Accordingly, a miniaturized column device is formed having a flow path extending from the first end 16 of the sample processing compartment and passing to the second end 20 thereof, whereby liquid phase analysis of samples may be carried out using techniques well known in the art.

Referring still to FIGS. 1–4, a particular embodiment of the invention is shown comprising sample introduction means laser-ablated into both the substrate 4 and cover plate 12. An internally ablated by-pass channel 24 is formed in substrate 4, said channel 24 being disposed near the first end 16 of the sample processing compartment. Two additional apertures 26 and 28 are formed in cover plate 12 and are arranged to cooperate with first and second ends (indicated at 30 and 32 respectively) of the by-pass channel 24. In this manner, a sample being held in an external reservoir may be introduced into by-pass channel 24 to form a sample plug of a known volume (defined by the dimensions of the channel 24). The sample plug thus formed may then be introduced into the first end 16 of the sample processing compartment 14 via inlet port 18 by communicating external mechanical valving with said inlet port and laser-ablated apertures 26 and 28 and flushing solution through the by-pass channel 24 into the sample processing compartment.

It is noted that the ablated by-pass channel 24 and apertures 26 and 28 further enable a wide variety of sample introduction techniques to be practiced according to the invention. Particularly, having a by-pass channel which is not connected to the sample processing compartment allows a user to flush a sample through the by-pass channel without experiencing sample carry-over or column contamination. As will be appreciated by one of ordinary skill in the art after reading this specification, one such sample introduction technique may be effected by butt-coupling an associated rotor to a stator (not shown) on the external surface of a miniaturized column where the rotor selectively interfaces external tubing and fluid sources with inlet port 18 and apertures 26 and 28, allowing a sample to be flushed from the by-pass channel 24 into external tubing from which the sample may then be introduced into the column via inlet port 18 for liquid phase analysis thereof. In this regard, a miniaturized column device formed in a polyimide substrate enables a ceramic rotor, pressed to the devices using tensioned force (to form a liquid-tight seal), to still rotate between selected aperture positions on the device due to the friction characteristics of the two materials. Other suitable rotors can be formed in rigid materials such as, but not limited to, glass and non-conductive substrates.

Accordingly, in the practice of the invention, external hardware provides the mechanical valving necessary for communication of a miniaturized column device to different external liquid reservoirs, such as an electrolyte solution, flush solution or the sample via laser-ablated holes designed into the cover plate 12. This feature allows a variety of injection methods to be adapted to a miniaturized planar column device constructed according to the invention, including pressure injection, hydrodynamic injection or electrokinetic injection. In the particular embodiment of FIGS. 1–3, it is contemplated that external valving and injection means communicate with the sample processing device by butt-coupling to the laser-ablated apertures, however, any other suitable methods of connection known in the art may easily be adapted to the invention. Further, it is noted that numerous other sample introduction and fluid interfacing designs may be practiced and still fall within the spirit of the subject invention.

Also according to the invention, a wide variety of means for applying a motive force along the length of the sample processing compartment 14 may be associated with the subject device. In this regard, a pressure differential or electric potential may be applied along the entire length of the sample processing compartment by interfacing motive means with inlet port 18 and outlet port 22.

The use of substrates such as polyimides in the construction of miniaturized columns according to the invention allows the possibility of using refractive-index (RI) detection to detect separated analytes of interest passing through the subject columns. In this regard, the provision of an associated laser diode which emits radiation at a wavelength where polyimide is "transparent" (such as at >500 nm) allows for a detection setup where no additional features need to be ablated in the column devices.

Referring now to FIGS. 2–4, in a preferred embodiment of the invention, detection means may be ablated into the substrate 4 and cover plate 12, where said detection means is disposed substantially downstream of the first end 16 of the sample processing compartment 14. More particularly, an aperture 34 may be ablated through substrate 4 to communicate with the sample processing compartment 14. A corresponding aperture 36 may be likewise formed in cover plate 12, and arranged so that it will be in co-axial alignment with aperture 34 when the cover plate is affixed to the substrate to form the sample processing compartment 14. In this manner, electrodes (not shown) may be connected to the miniaturized column device via the apertures 34 and 36 to detect separated analytes of interest passing through the sample processing compartment by electrochemical detection techniques.

Figure 5:
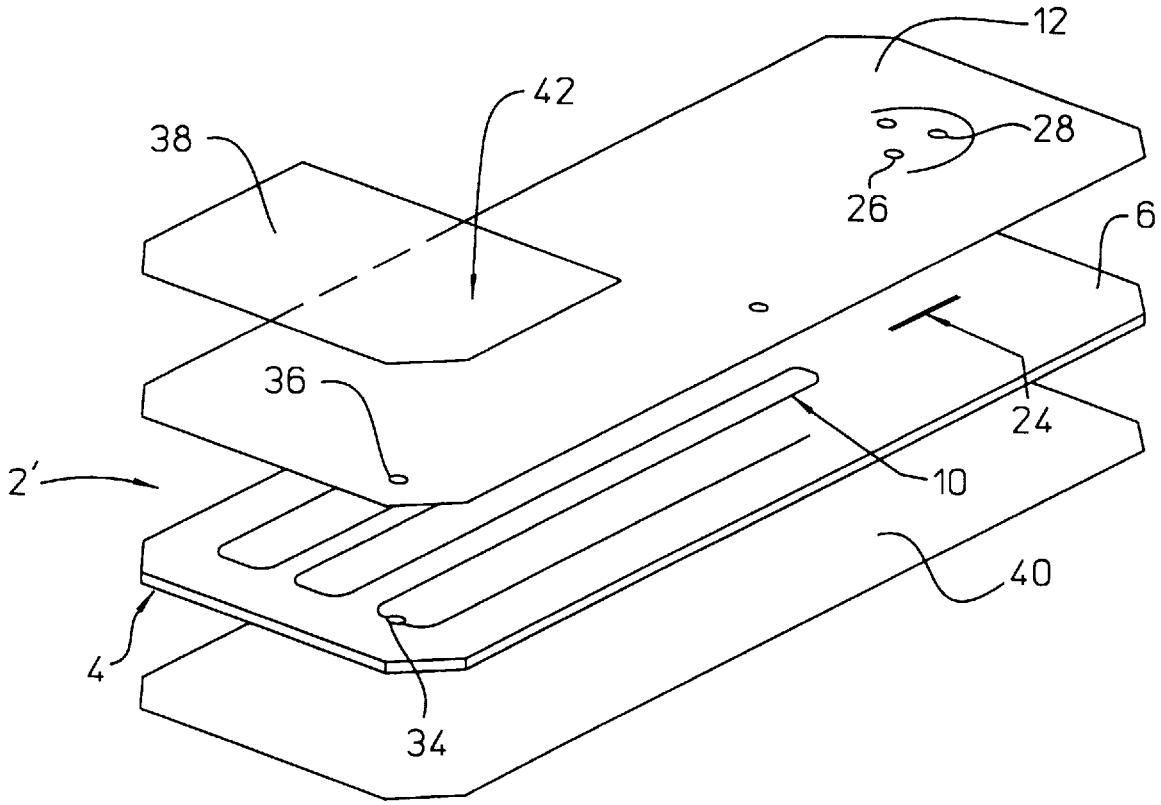
FIG. 5 is an exploded view of a preferred embodiment of the present invention including optical detection means.

Referring to FIG. 5, a further embodiment of the invention, indicated at 2' is shown comprising a preferred detection means indicated generally at 42. More particularly, a first transparent sheet 38 is provided wherein the cover plate 12 is interposed between said first transparent sheet and substrate 4. A second transparent sheet 40 is also provided wherein the second sheet is disposed over the second planar surface 8 of the substrate 4. In this manner, detection means 42 allows optical detection of separated analytes passing through sample processing compartment, formed by the combination of microchannel 10 and cover plate 12, via transmission of radiation orthogonal to the major axis of the sample processing compartment (and, accordingly, orthogonal to the direction of electro-osmotic flow in an electrophoretic separation). Further, in the practice of the invention, the transparent sheets may comprise materials such as quartz, diamond, sapphire, fused silica or any other suitable substrate which enables light transmission therethrough.

The subject transparent sheets may be formed with just enough surface area to cover and seal the detection apertures 34 and 36, or said sheets may be sized to cover up to the entire surface area of the column device. In this regard, additional structural rigidity may be provided to a column device formed in a particularly thin substrate film, such as a thin-film polyimide substrate, by employing a substantially co-planar sheet of, for example, fused silica.

Accordingly, the above described optical detection means 42 enables adaptation of a variety of external optical detection means to miniaturized columns constructed according to the invention. Further, sealing of the transparent sheets 38 and 40 to the miniaturized column device 2' is readily enabled, for example, when substrate 4 and cover plate 12 are formed in polyimide materials which include a layer of a thermal adhesive form of polyimide, since it is known that quartz/Kapton® bonds formed using such adhesives are very resilient. Sealing of other preferred transparent sheet materials, such as diamond, sapphire or fused-silica to the subject device may be accomplished using adhesion techniques well known in the art.

The possibility of detecting with radiation over a range of electromagnetic wavelengths offers a variety of spectrophotometric detection techniques to be interfaced with a miniaturized column according to the invention, including UV/Vis, fluorescence, refractive index (RI) and Raman.

Furthermore, as will be readily appreciated, the use of optical detection means comprising apertures ablated into the substrate and cover plate provides great control over the effective detection path length in a miniaturized column device constructed according to the invention. In this regard, the detection path length will be substantially equal to the combined thickness of the substrate 4 and the cover plate 12, and detection path lengths of up to 250 $\mu$m are readily obtainable using the subject detection means 42 in thin-film substrates such as polyimides.

Figure 6:
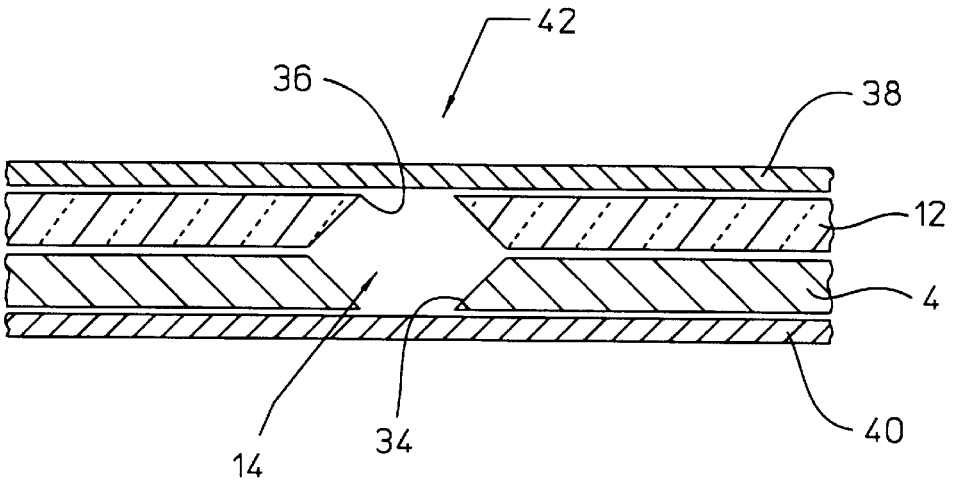
FIG. 6 is a cross-sectional axial view of the intersection of the sample processing compartment and the optical detection means in the miniaturized column device of FIG. 5.

Referring now to FIG. 6, it can be seen that apertures 34 and 36 provide an enlarged volume in sample processing compartment 14 at the point of intersection with the detection means 42, where that volume will be proportional to the combined thickness of substrate 4 and cover plate 12. In this manner, sample plugs passing through sample processing compartment 14 may be subject to untoward distortion as the plug is influenced by the increased compartment volume in the detection area, especially where the combined thickness of the substrate and cover plate exceeds about 250 $\mu$m, thereby possibly reducing separation efficiency in the device.

Accordingly, in the present invention wherein detection path lengths exceeding 250 $\mu$m are desired, an alternative device embodiment is provided having laser-ablated features on two opposing surfaces of a substrate. More particularly, in FIGS. 7A and 7B, a further embodiment of a miniaturized column device is generally indicated at 52. The miniaturized column comprises a substrate 54 having first and second substantially planar opposing surfaces respectively indicated at 56 and 58. The substrate 54 has a first microchannel 60 laser ablated in the first planar surface 56 and a second microchannel 62 laser ablated in the second planar surface 58, wherein the microchannels can be provided in a wide variety of geometries, configurations and aspect ratios as described above.

Figure 7A:
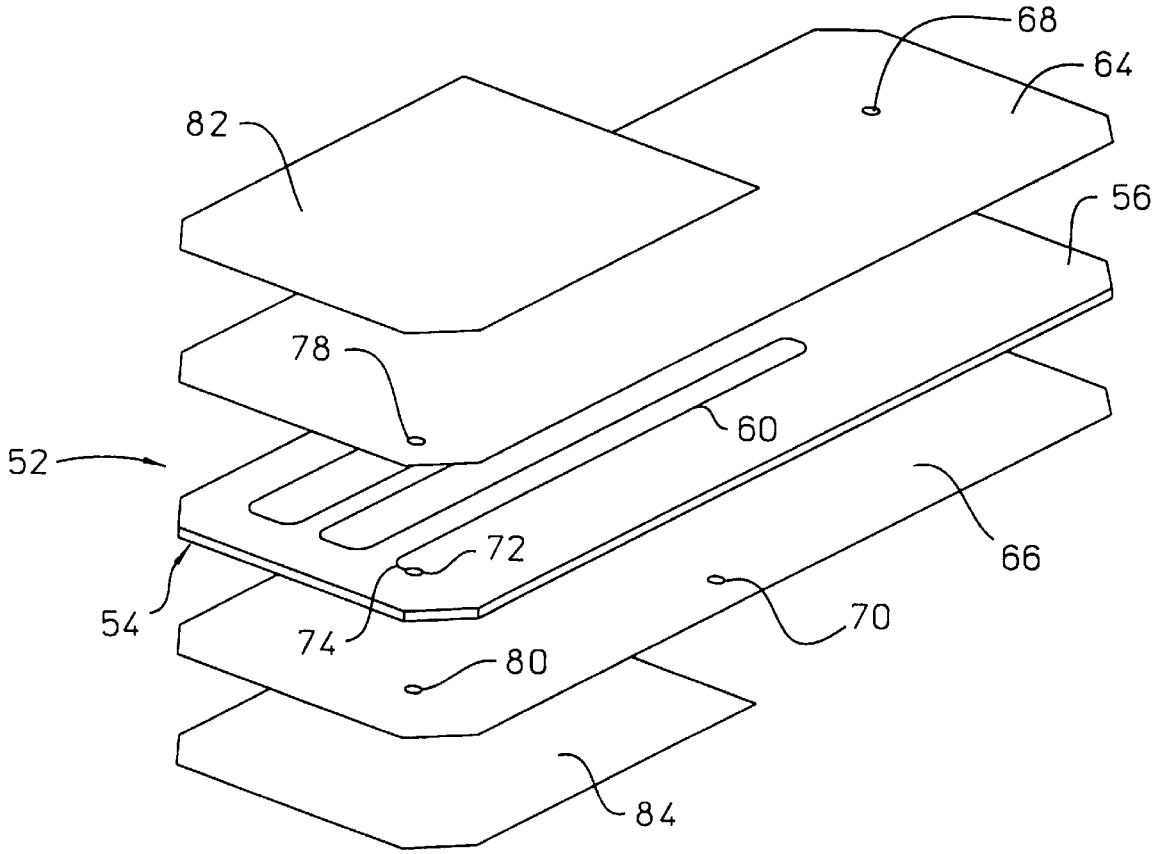
FIG. 7A is an exploded view of a first side of a miniaturized column device having microchannels formed on two opposing planar surfaces of a support substrate.
Figure 7B:
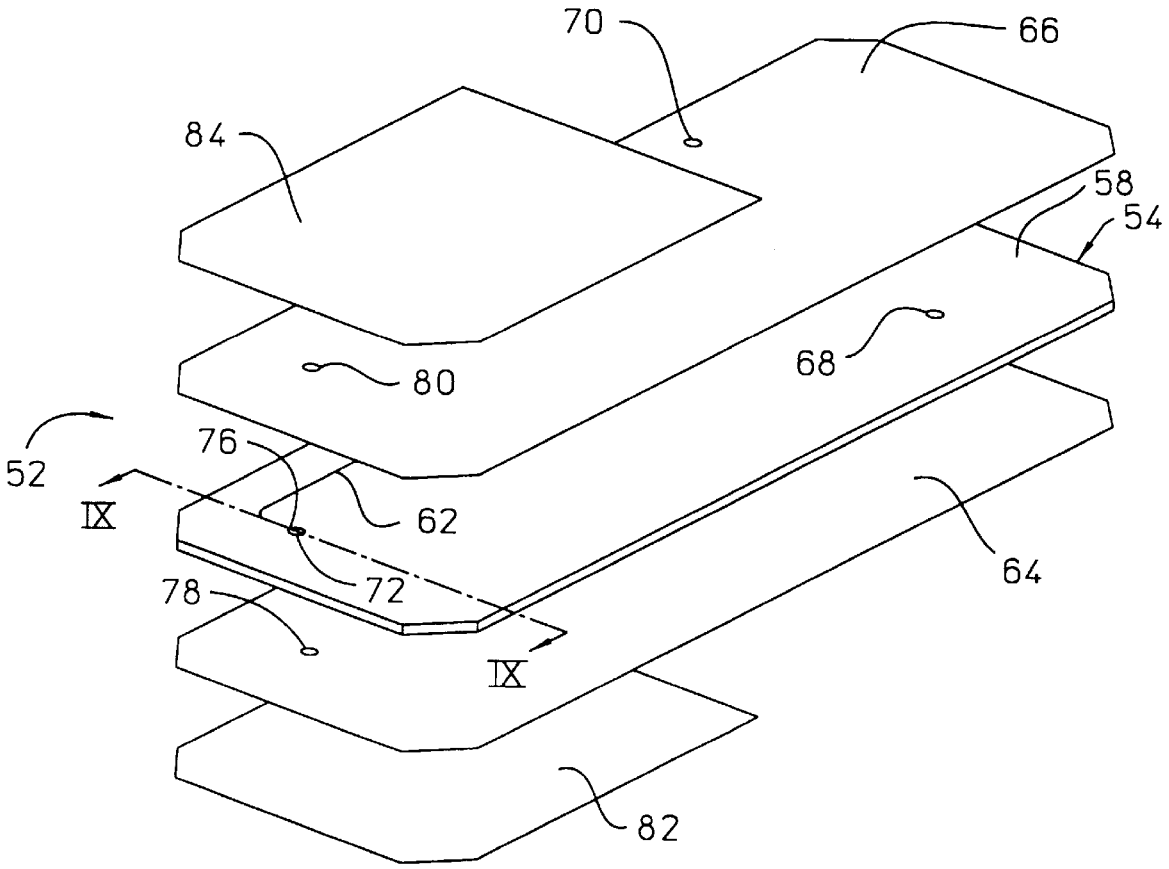
FIG. 7B is an exploded view of a second side of the column device of FIG. 7A.

The miniaturized column device of FIGS. 7A and 7B further includes first and second cover plates, indicated at 64 and 66 respectively, which, in combination with the first and second microchannels 60 and 62, define first and second elongate separation compartments when substrate 54 is sandwiched between the first and second cover plates.

Referring still to FIGS. 7A and 7B, a plurality of apertures can be laser-ablated in the device to provide an extended separation compartment, and further to establish fluid communication means. More particularly, a conduit means 72, comprising a laser ablated aperture in substrate 54 having an axis which is orthogonal to the first and second planar surfaces 56 and 58, communicates a distal end 74 of the first microchannel 60 with a first end 76 of the second microchannel 62 to form an extended separation compartment.

Further, an aperture 68, laser ablated in the first cover plate 64, enables fluid communication with the first microchannel 60, and a second aperture 70, laser ablated in the second cover plate 66, enables fluid communication with the second microchannel 62. As will be readily appreciated, when the aperture 68 is used as an inlet port, and the second aperture 70 is used as an outlet port, a miniaturized column device is provided having a flow path extending along the combined length of the first and second microchannels 60 and 62.

In the embodiment of the invention as shown in FIGS. 7A and 7B, a wide variety of sample introduction means can be employed, such as those described above. External hardware can also be interfaced to the subject device to provide liquid handling capabilities, and a variety of means for applying a motive force along the length of the separation compartment can be associated with the device, such as by interfacing motive means with the first and/or second apertures 68 and 70 as described above.

Additionally, a variety of detection means are easily included in the subject embodiment. In this regard, a first aperture 78 can be laser ablated in the first cover plate 64, and a second aperture 80 can likewise be formed in the second cover plate 66 such that the first and second apertures will be in co-axial alignment with conduit means 72 when the substrate 54 is sandwiched between the first and second cover plates. Detection of analytes in a separated sample passing through the conduit means is thereby easily enabled, such as by connecting electrodes to the miniaturized column via apertures 78 and 80 and detecting using electrochemical techniques.

Figure 9:
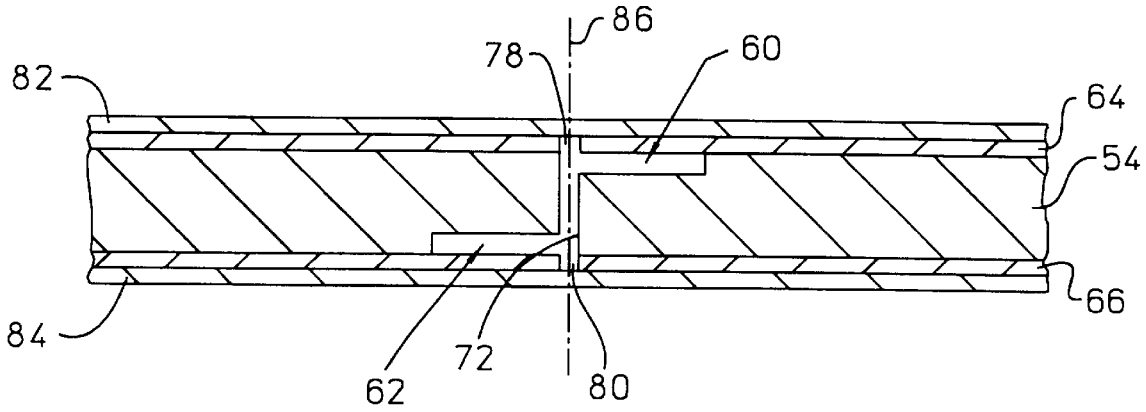
FIG. 9 is a cross-sectional trans-axial view of the extended optical detection path length in the miniaturized column of FIG. 8 taken along lines IX—IX.

However, a key feature of the laser-ablated conduit means 72 is the ability to provide an extended optical detection path length of up to 1 mm, or greater, without experiencing untoward sample plug distortion due to increased separation compartment volumes at the point of detection. Referring to FIGS. 7A, 7B and 9, first and second transparent sheets, indicated at 82 and 84 respectively, can be provided such that the first cover plate 64 is interposed between the first transparent sheet and the first planar surface 56, and the second cover plate 66 is interposed between the second transparent sheet and the second planar surface 58. The transparent sheets 82 and 84 can be selected from appropriate materials such as quartz crystal, fused silica, diamond, sapphire and the like. Further, the transparent sheets can be provided having just enough surface area to cover and seal the apertures 78 and 80, or those sheets can be sized to cover up to the entire surface area of the column device. As described above, this feature allows additional structural rigidity to be provided to a column device formed in a particularly thin substrate.

As best shown in FIG. 9, the subject arrangement allows optical detection of sample analytes passing through the miniaturized column device to be carried out along an optical detection path length 86 corresponding to the major axis of the conduit means 72. As will be readily appreciated, the optical detection path length 86 is substantially determined by the thickness of the substrate 54, and, accordingly, a great deal of flexibility in tailoring a miniaturized column device having $\mu$-meter column dimensions and optical path lengths of up to 1 mm or greater is thereby enabled under the instant invention. In this manner, a wide variety of associated optical detection devices may be interfaced with a miniaturized column constructed according to the invention, and detection of analytes in samples passing through the conduit means 72 may be carried out using UV/Vis, fluorescence, refractive index (RI), Raman and like spectrophotometric techniques.

Figure 8A:
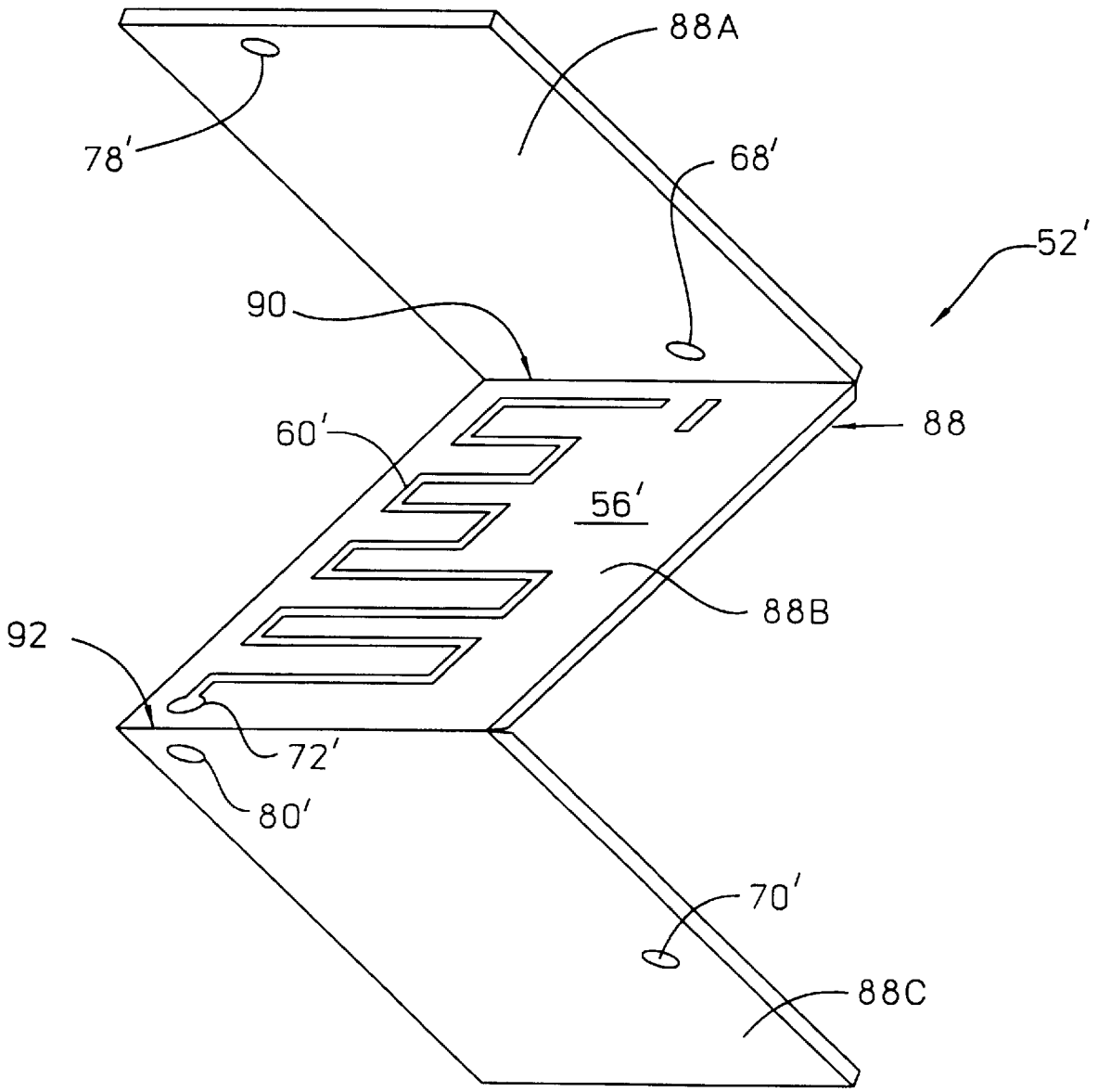
FIG. 8A is a pictorial representation of a first side of a preferred embodiment of the miniaturized column device of FIG. 7A which is constructed from a single flexible substrate.
Figure 8B:
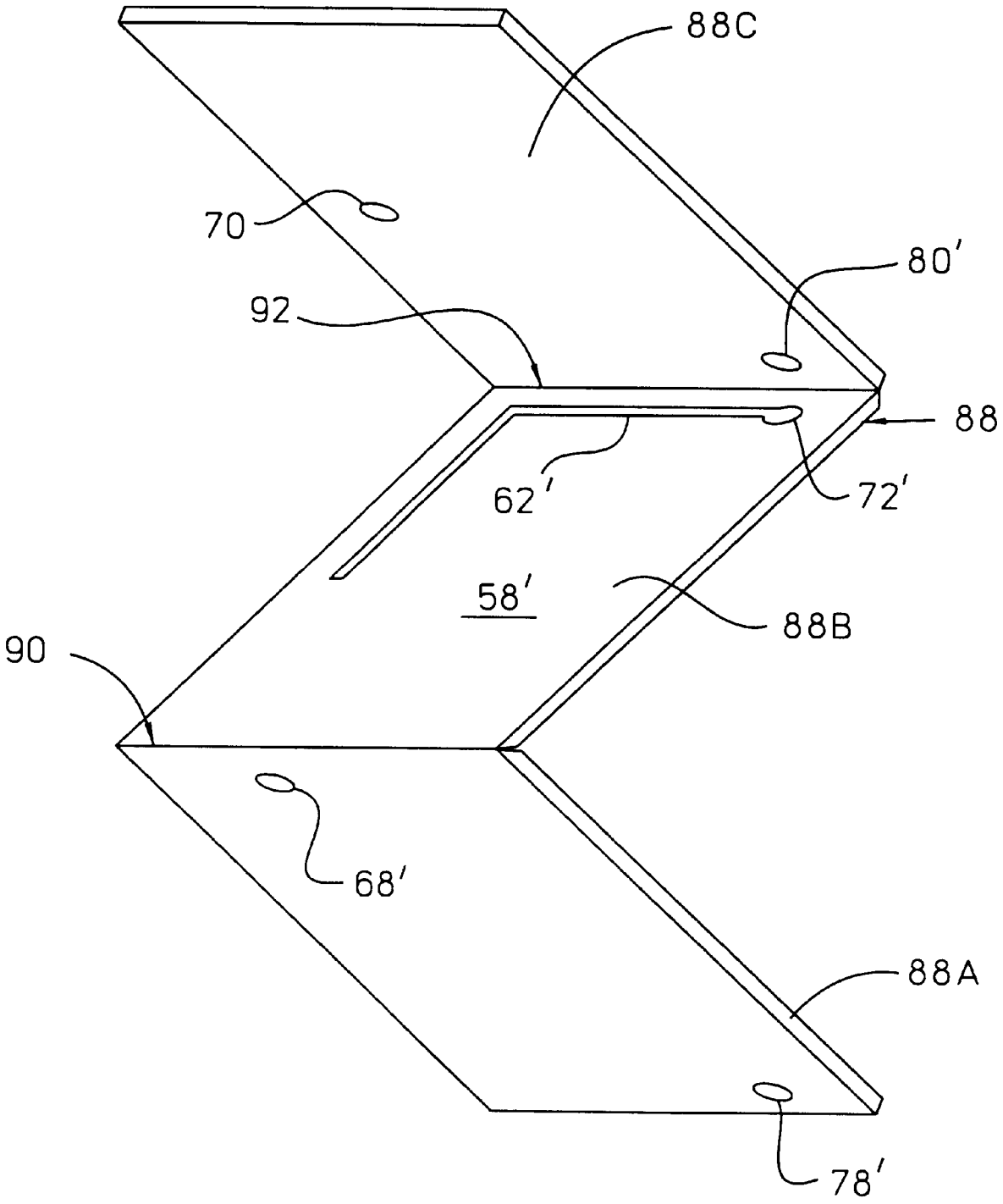
FIG. 8B is a pictorial representation of a second side of the column device of FIG. 8A.

Referring now to FIGS. 8A and 8B, a related embodiment of the invention is shown, comprising a miniaturized column device 52', wherein the column portion and the first and second cover plates are formed in a single, flexible substrate generally indicated at 88. The flexible substrate 88 thus comprises three distinct regions, a column portion 88B, having first and second substantially planar opposing surfaces 56' and 58', respectively, where the column portion is interposed between a first cover plate portion 88A and a second cover plate portion 88C. The first and second cover plate portions have at least one substantially planar surface. The first cover plate portion 88A and the column portion 88B are separated by at least one fold means 90 such that the first cover plate portion can be readily folded to overlie the first substantially planar surface 56' of the column portion 88B. The second cover plate portion 88C and the column portion 88B are likewise separated by at least one fold means 92 such that the second cover plate can be readily folded to overlie the second substantially planar surface 58' of the column portion 88B. In particularly preferred embodiments, each fold means 90 and 92 can comprise a row of spaced-apart perforations ablated in the flexible substrate, spaced-apart slot-like depressions or apertures ablated so as to extend only part way through the substrate, or the like. The perforations or depressions can have circular, diamond, hexagonal or other shapes that promote hinge formation along a predetermined straight line.

Thus, the miniaturized column device 52' is formed by laser ablating a first microchannel 60' in the first planar surface 56' of the column portion 88B, and a second microchannel 62' in the second planar surface 58' of the column portion. Each microchannel can be provided in a wide variety of geometries, configurations and aspect ratios. A first separation compartment is then formed by folding the flexible substrate 88 at the first fold means 90 such that the first cover plate portion 88A covers the first microchannel 60' to form an elongate separation compartment. A second separation compartment is then provided by folding the flexible substrate 88 at the second fold means 92 such that the second cover plate portion 88C covers the second microchannel 62' to form a separation compartment as described above. A conduit means 72', comprising a laser ablated aperture in the column portion 88B having an axis which is orthogonal to the first and second planar surfaces 56' and 58', communicates a distal end of the first microchannel 60' with a first end of the second microchannel 62' to form a single, extended separation compartment.

Further, an aperture 68', laser ablated in the first cover plate portion 88A, enables fluid communication with the first microchannel 60', and a second aperture 70', laser ablated in the second cover plate portion 88C, enables fluid communication with the second microchannel 62'. As described above, when the first and second apertures are used as an inlet and outlet port, respectively, a miniaturized column device is provided having a flow path extending along the combined length of the first and second microchannels.

Detection means can optionally be included in the device of FIGS. 8A and 8B. In one particular embodiment, a first aperture 78' can be laser ablated in the first cover plate portion 88A, and a second aperture 80' can likewise be formed in the second cover plate portion 88C, wherein the apertures are arranged to co-axially communicate with each other and communicate with the conduit means 72' when the flexible substrate 88 is hingeably folded as described above to accurately align the apertures 78' and 80' with the conduit means 72'.

In yet further related aspects of the invention, optional micro-alignment means—formed either by laser ablation techniques or by other methods of fabricating shaped pieces well known in the art—are provided in the miniaturized column device 52'. More specifically, a plurality of corresponding laser-ablated apertures (not shown) can be provided in the column portion 88B and the first and second cover plate portions, 88A and 88C, respectively of the flexible substrate 88. The subject apertures are arranged such that co-axial alignment thereof enables the precise alignment of the column portion with one, or both of the cover plate portions to align various features such as the optional detection means with the ablated conduit. Such optional alignment can be effected using an external apparatus with means (such as pins) for cooperating with the co-axial apertures to maintain the components are portions in proper alignment with each other.

Accordingly, novel miniaturized column devices have been described which are laser ablated into a substrate other than silicon or silicon dioxide materials, and which avoid several major problems which have come to be associated with prior attempts at providing micro-column devices. The use of laser ablation techniques in the practice of the invention enables highly symmetrical and accurately defined micro-column devices to be fabricated in a wide class of polymeric and ceramic substrates to provide a variety of miniaturized liquid-phase analysis systems. In this regard, miniaturized columns may be provided which have microcapillary dimensions (ranging from 5–200 $\mu$m in diameter) and column detection path lengths of up to 1 mm or greater. This feature has not been attainable in prior attempts at miniaturization, such as in capillary electrophoresis, without substantial engineering of a device after capillary formation. Further, laser ablation of miniaturized columns in inert substrates such as polyimides avoids the problems encountered in prior devices formed in silicon or silicon dioxide-based materials. Such problems include the inherent chemical activity and pH instability of silicon and silicon dioxide-based substrates which limits the types of separations capable of being performed in those devices.

In the practice of the invention, miniaturized column devices may be formed by laser ablating a set of desired features in a selected substrate using a step-and-repeat process to form discrete units. In this regard, it is particularly contemplated to laser ablate the subject devices in condensation polymer substrates including polyimides, polyamides, poly-esters and poly-carbonates. Further, the instant invention may be practiced using either a laser ablation process or a LIGA process to form templates encompassing a set of desired features, whereby multiple copies of miniaturized columns may be mass-produced using injection molding techniques well known in the art. More particularly, it is contemplated herein to form miniaturized columns by injection molding in substrates comprised of materials such as the following: polycarbonates; polyesters, including poly (ethylene terephthalate) and poly(butylene terephthalate); polyamides, (such as nylons); polyethers, including polyformaldehyde and poly(phenylene sulfide); polyimides, such as Kapton® and Upilex®; polyolefin compounds, including ABS polymers, Kcl-F copolymers, poly(methyl methacrylate), poly(styrene-butadiene) copolymers, poly (tetrafluoroethylene), poly(ethylenevinyl acetate) copolymers, poly(N-vinylcarbazole) and polystyrene.

Laser ablation of microchannels in the surfaces of the above-described substrates has the added feature of enabling a wide variety of surface treatments to be applied to the microchannels before formation of the sample processing compartment. That is, the open configuration of laser-ablated microchannels produced using the method of the invention enables a number of surface treatments or modifications to be performed which are not possible in closed format constructions, such as in prior micro-capillaries. More specifically, laser ablation in condensation polymer substrates provides microchannels with surfaces featuring functional groups, such as carboxyl groups, hydroxyl groups and amine groups, thereby enabling chemical bonding of selected species to the surface of the subject microchannels using techniques well known in the art. Other surface treatments enabled by the open configuration of the instant devices include surface adsorptions, polymer graftings and thin film deposition of materials such as diamond or sapphire to microchannel surfaces using masking and deposition techniques and dynamic deactivation techniques well known in the art of liquid separations.

The ability to exert rigid computerized control over the present laser ablation processes enables extremely precise microstructure formation, which, in turn, enables the formation of miniaturized columns having features ablated in two substantially planar components wherein those components may be aligned to define a composite sample processing compartment of enhanced symmetry and axial alignment. In this regard, it is contemplated to provide a further embodiment of the invention wherein laser ablation is used to create two component halves which, when folded or aligned with one another, define a single miniaturized column device.

Figure 10:
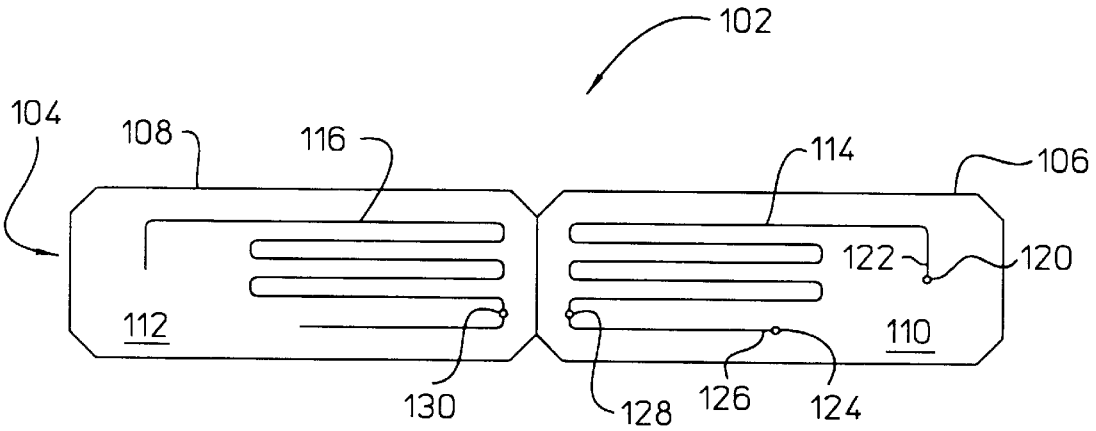
FIG. 10 is plan view of a miniaturized column device constructed according to the invention having first and second component halves.

Referring now to FIG. 10, a miniaturized column for liquid phase analysis of a sample is generally indicated at 102. The miniaturized column 102 is formed by providing a support body 104 having first and second component halves indicated at 106 and 108 respectively. The support body may comprise a substantially planar substrate such as a polyimide film which is both laser ablatable and flexible so as to enable folding after ablation; however, the particular substrate selected is not considered to be limiting in the invention.

The first and second component halves 106 and 108 each have substantially planar interior surfaces, indicated at 110 and 112 respectively, wherein miniaturized column features may be laser ablated. More particularly, a first microchannel pattern 114 is laser ablated in the first planar interior surface 110 and a second microchannel pattern 116 is laser ablated in the second planar interior surface 112. According to the invention, said first and second microchannel patterns are ablated in the support body 104 so as to provide the mirror image of each other.

Figure 11:
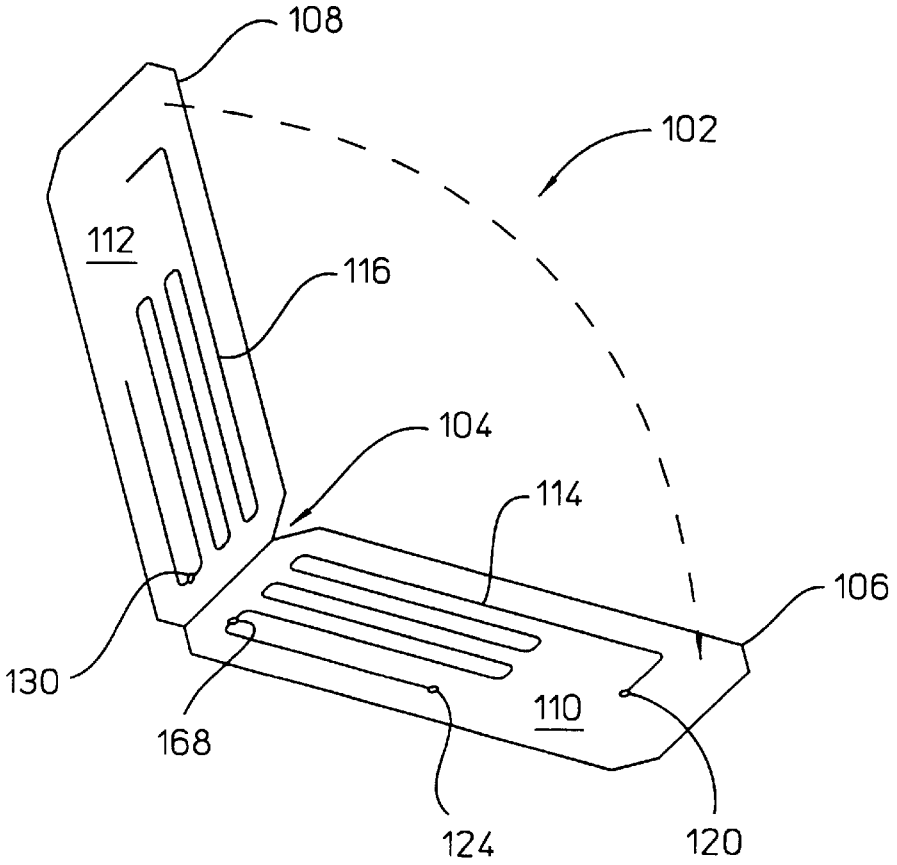
FIG. 11 is a pictorial representation of the column device of FIG. 10 showing the folding alignment of the component halves to form a single device.
Figure 12:
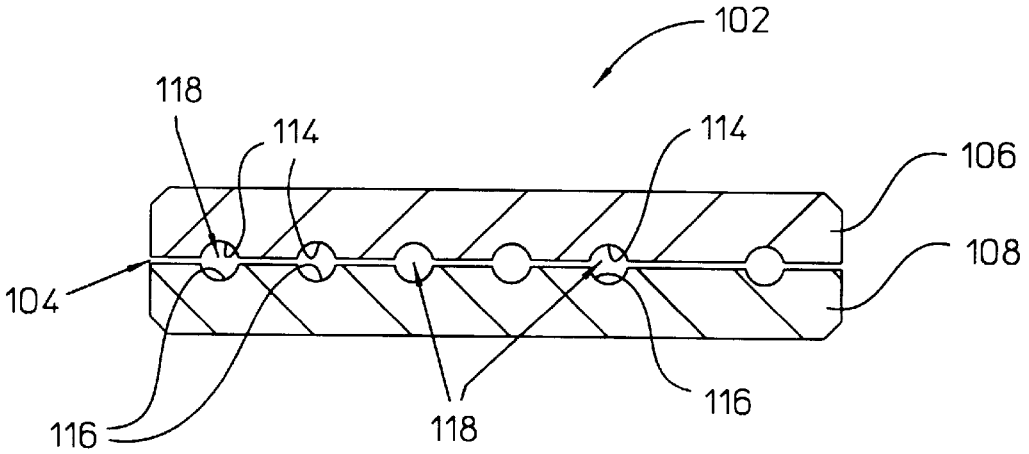
FIG. 12 is a cross-sectional axial view of the sample processing compartment formed by the alignment of the component halves in the device of FIG. 10.

Referring now to FIGS. 11 and 12, a sample processing compartment 118, comprising an elongate bore defined by the first and second microchannel patterns 114 and 116 may be formed by aligning (such as by folding) the first and second component halves 106 and 108 in facing abutment with each other. In the practice of the invention, the first and second component halves may be held in fixable alignment with one another to form a liquid-tight sample processing compartment using pressure sealing techniques, such as by application of tensioned force, or by use of adhesives well known in the art of liquid phase separation devices. It is further contemplated according to the invention to form first and second mirochannels 114 and 116 having semi-circular cross-sections whereby alignment of the component halves defines a sample processing compartment 118 having a highly symmetrical circular cross-section to enable enhanced fluid flow therethrough; however, as discussed above, a wide variety of microchannel geometries are also within the spirit of the invention.

In a further preferred embodiment of the invention, it is particularly contemplated to form the support body 104 from a polymer laminate substrate comprising a Kapton® film co-extruded with a thin layer of a thermal plastic form of polyimide referred to as KJ® and available from DuPont (Wilmington, Del.). In this manner, the first and second component halves 106 and 108 may be heat sealed together, resulting in a liquid-tight weld that has the same chemical properties and, accordingly, the same mechanical, electrical and chemical stability, as the bulk Kapton® material.

Referring now to FIGS. 10–12, the miniaturized column device 102 further comprises means for communicating associated external fluid containment means (not shown) with the sample processing compartment 118 to provide a liquid-phase separation device. More particularly, a plurality of apertures may be laser ablated in the support body 104, wherein said apertures extend from at least one exterior surface of the support body and communicate with at least one microchannel, said apertures permitting the passage of fluid therethrough. In this regard, an inlet port 120 may be laser ablated in the first component half 106 and communicate with a first end 122 of said first microchannel 114. In the same manner, an outlet port 124 may be ablated in the first component half and communicate with a second end 126 of said first microchannel 114.

As is readily apparent, a liquid phase sample processing device may thereby be formed, having a flow path extending from the first end 122 of the microchannel 114 to the second end 126 thereof, by communicating fluids from an associated source (not shown) through the inlet port 120, passing the fluids through the sample processing compartment 118 formed by the alignment of microchannels 114 and 116, and allowing the fluids to exit the sample processing compartment via the outlet port 126. In this manner, a wide variety of liquid phase analysis procedures may be carried out in the subject miniaturized column device using techniques well known in the art. Furthermore, various means for applying a motive force along the length of the sample processing compartment 118, such as a pressure differential or electric potential, may be readily interfaced to the column device via the inlet and outlet ports, or by interfacing with the sample processing compartment via additional apertures which may be ablated in the support body 104.

Inlet port 120 may be formed such that a variety of external fluid and/or sample introduction means may be readily interfaced with the miniaturized column device 102. As discussed in greater detail above, such means include external pressure injection, hydrodynamic injection or electrokinetic injection mechanisms.

Referring now to FIGS. 10 and 11, the miniaturized column device 102 further comprises detection means laser ablated in the support body 104. More particularly, a first aperture 128 is ablated in said first component half 106 and communicates with the first microchannel 114 at a point near the second end 126 thereof. A second aperture 130 is likewise formed in said second component half 108 to communicate with the second microchannel 116. Accordingly, a wide variety of associated detection means may then be interfaced to the sample processing compartment 118 to detect separated analytes of interest passing therethrough, such as by connection of electrodes to the miniaturized column via the first and second apertures 128 and 130.

In yet a further preferred embodiment of the invention, an optical detection means is provided in the miniaturized column device 102. In this regard, first and second apertures 128 and 130 may be ablated in the support body 104 such that when the component halves are aligned to form the sample processing compartment 118 said apertures are in co-axial alignment with one another, said apertures further having axes orthogonal to the plane of said support body. As will be readily appreciated by one of ordinary skill in the art, by providing transparent sheets (not shown), disposed over the exterior of the support body 104 and covering said first and second apertures 128 and 130, a sample passing through sample processing compartment 118 may be analyzed by interfacing spectrophotometric detection means with said sample through the transparent sheets using techniques well known in the art. The optical detection path length may be substantially determined by the combined thickness of said first and second component halves 106 and 108. In this manner, an optical detection path length of up to 250 $\mu$m is readily provided by ablating the miniaturized column device in a 125 $\mu$m polymer film.

Accordingly, there have been described several preferred embodiments of a miniaturized column device formed according to the invention by laser ablating microstructures on component parts and aligning the components to form columns having enhanced symmetries. As described in detail above, formation of the subject microchannels in the open configuration enables a wide variety of surface treatments and modifications to be applied to the interior surfaces of the channels before formation of the sample processing compartment. In this manner, a wide variety of liquid phase analysis techniques may be carried out in the composite sample processing compartments thus formed, including chromatographic, electrophoretic and electrochromatographic separations.

In the practice of the invention, it is further contemplated to provide optional means for the precise alignment of component support body halves, thereby ensuring accurate definition of a composite sample processing compartment formed according to the invention. More particularly, in a further preferred embodiment of the invention, micro-alignment means are provided to enable enhanced alignment of laser-ablated component parts such as microchannels, detection apertures and the like.

Figure 13:
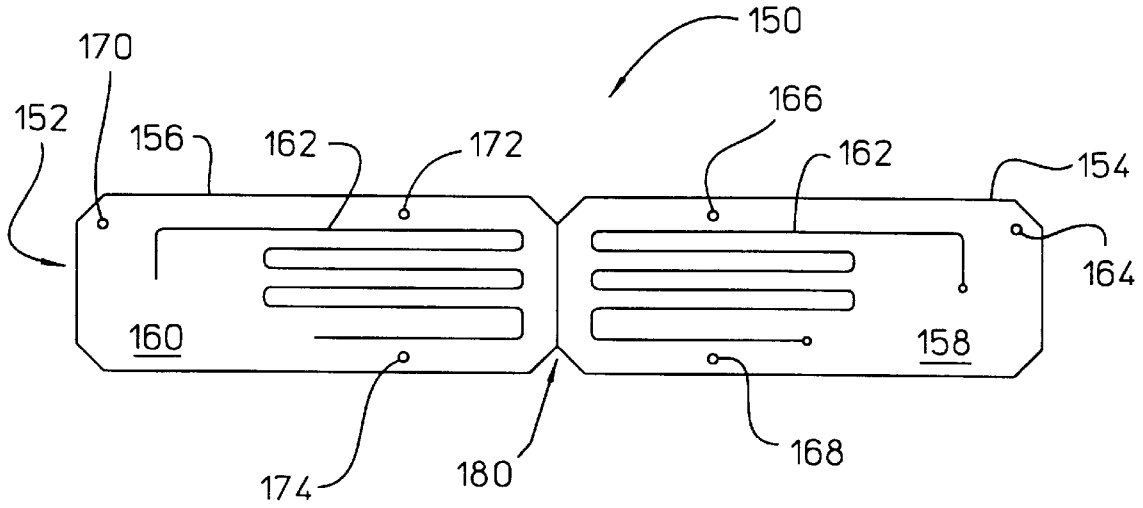
FIG. 13 is a plan view of a further preferred embodiment of the present invention having optional micro-alignment means on first and second component halves.
Figure 14:
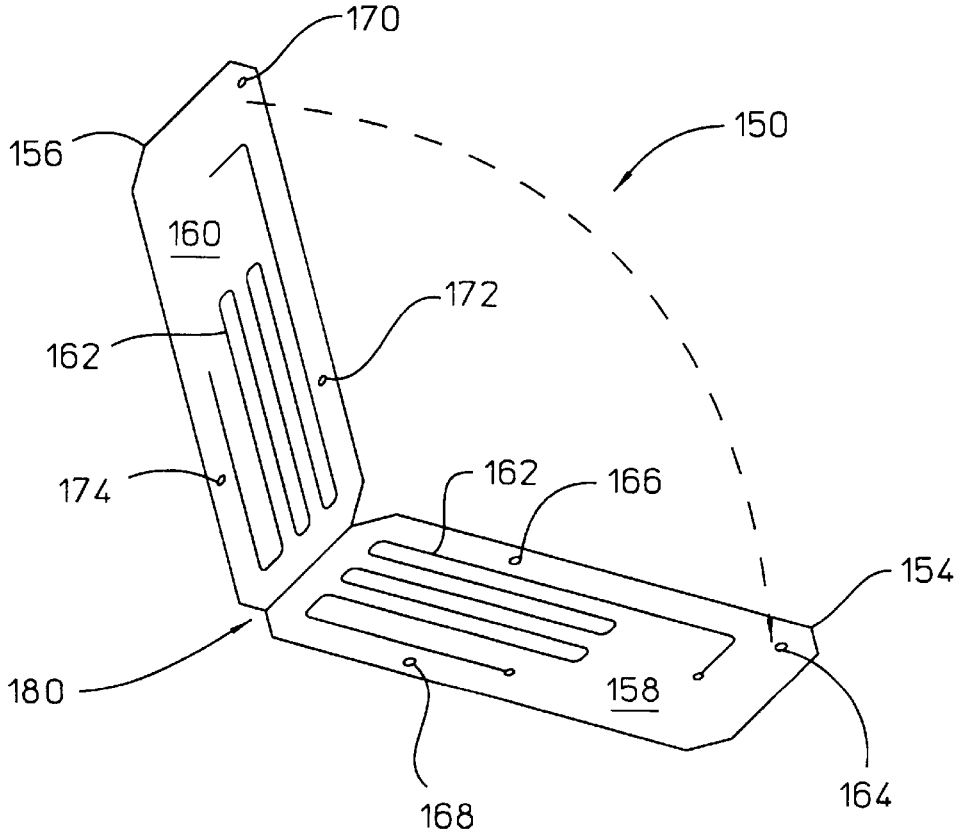
FIG. 14 is a pictorial representation of the column device of FIG. 13 showing the micro-alignment of the component halves.

Referring now to FIGS. 13 and 14, a miniaturized column device constructed according to the present invention is generally indicated at 150 and is formed in a flexible substrate 152. The column device comprises first and second support body halves, indicated at 154 and 156 respectively, each having a substantially planar interior surface indicated at 158 and 160 respectively. The interior surfaces comprise laser-ablated microstructures, generally indicated at 162, where said microstructures are arranged to provide the mirror image of one another in the same manner as described in greater detail above.

The accurate alignment of component parts may be enabled by forming a miniaturized column device in a flexible substrate 152 having at least one fold means, generally indicated at 180, such that a first body half 154 may be folded to overlie a second body half 156. The fold means 180 may comprise a row of spaced-apart perforations ablated in the substrate 152, spaced-apart slot-like depressions or apertures ablated so as to extend only part way through the substrate, or the like. The perforations or depressions may have circular, diamond, hexagonal or other shapes that promote hinge formation along a predetermined straight line.

Accordingly, in the practice of the invention, the fold means 180 allows said first and second support body halves 154 and 156 to hingeably fold upon one another and accurately align composite features defined by said microstructures ablated on said first and second planar interior surfaces 158 and 160.

It is further contemplated to provide additional micro-alignment means formed either by laser ablation or by other methods of fabricating shaped pieces well known in the art. More specifically, a plurality of laser-ablated apertures (not shown) may be provided in said first and second support body halves 154 and 156 where said apertures are so arranged such that co-axial alignment thereof enables the precise alignment of the support body halves to define composite features such as an ablated elongate bore. Alignment may be effected using an external apparatus with means (such as pins) for cooperating with said co-axial apertures to maintain the body halves in proper alignment with one another.

Referring to FIGS. 13 and 14, in yet another particular embodiment of the invention, micro-alignment means may been formed in said first and second support body halves 154 and 156 using fabrication techniques well known in the art e.g., molding or the like. In this manner, a plurality of projections, indicated at 164, 166 and 168, may be formed in said first support body half 154. A plurality of depressions, indicated at 170, 172 and 174, may be formed in said second support body half 156.

Accordingly, as is readily apparent, the micro-alignment means are configured to form corresponding structures with one another, whereby projection 164 mates with depression 170, projection 166 mates with depression 172, and projection 168 mates with depression 174 when said support body halves are aligned in facing abutment with one another. In this manner, positive and precise alignment of support body halves 154 and 156 is enabled, thereby accurately defining composite features defined by said laser-ablated microstructures 162.

As will be readily apparent to one of ordinary skill in the art after reading this specification, a wide variety of corresponding micro-alignment features may be formed in the subject miniaturized column devices without departing from the spirit of the instant invention. Such additional features include any combination of holes and/or corresponding structures such as grooves and ridges in said component parts where said features cooperate to enable precise alignment of the component body parts.

Figure 15:
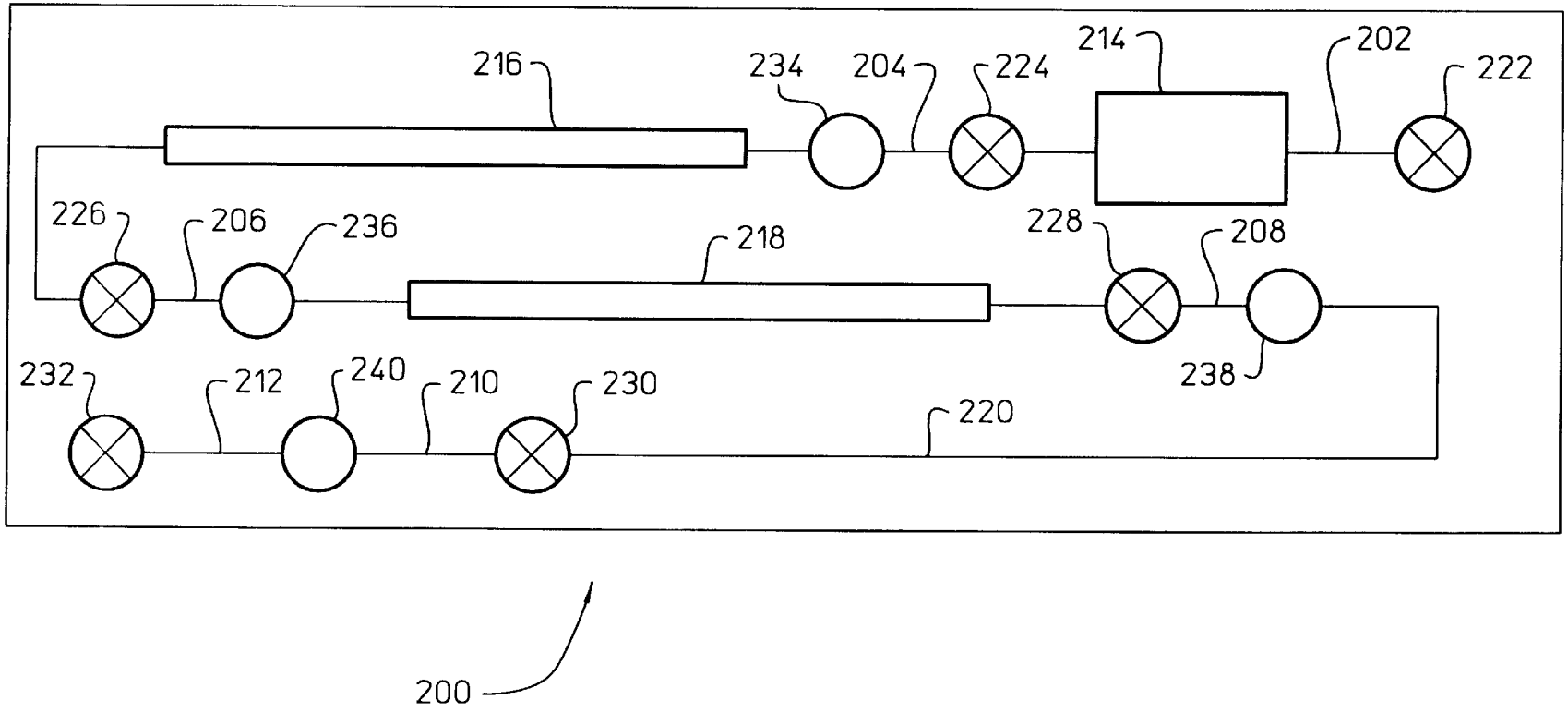
FIG. 15 is a diagram of an exemplary $\mu$-TAS.

FIG. 15 illustrates one embodiment of a $\mu$-TAS. While this embodiment is described for bioanalytical applications (see Example 1), it an object of the invention to provide start-to-finish analysis for any solute species, including small (less than about 1000 molecular weight) solute species in complex matrices.

Generally, $\mu$-TAS 200 can be constructed as described in detail above by providing a substrate having first and second planar opposing surfaces and laser ablating a microchannel having more than one sample handling region (202 through 212 and 214 through 220) in the first planar substrate, and optionally having a plurality of laser-ablated access ports (222 through 232) and detection means (234 through 240). A sample processing compartment having sample flow components (202 through 212) and sample treatment components (214 through 220) corresponding to the sample handling regions can be formed by arranging a cover plate over the planar surface (see, e.g., FIGS. 1–4).

Alternatively, $\mu$-TAS 200 may be constructed by providing a support body having first and second component halves with planar interior surfaces, laser ablating mirror images of a microchannel having more than one sample handling region (202 through 212 and 214 through 220) in the interior surfaces of the first and second component interior surfaces, and optionally having laser-ablated access ports (222 through 232) and detection means (234 through 240). A sample processing compartment having sample flow components (202 through 212) and sample treatment components (214 through 220) may be formed by aligning the interior surfaces in facing abutment with each other (see, e.g., FIGS. 10–12).

In a further embodiment, $\mu$-TAS 200 may be constructed as described above in reference to FIGS. 8A and 8B by providing a single, flexible substrate having three distinct regions, a column portion, having first and second substantially planar opposing surfaces, a first cover plate portion and a second cover plate portion. Thus, for example, a microchannel having more than one sample handling region (202 through 212 and 214 through 220) can be laser ablated in the first planar surface of the column portion of the flexible substrate. A sample processing compartment is then formed by folding the flexible substrate at the first fold means such that the first cover plate portion covers the first planar surface of the column portion. Alternatively, mirror images of a microchannel having more than one sample handling region (202 through 212 and 224 through 220) can be laser ablated in the first planar surface of the column portion and the interior surface of the first cover portion of the flexible substrate such that a sample processing compartment is formed by folding the flexible substrate at the first fold means as described above by aligning the first planar surface of the column portion with the interior surface of the first cover portion in facing abutment with each other.

Generally, the sample handling region of the microchannel from which the sample flow components (202 through 222) are formed is elongate and semi-circular in geometry. However, as described in greater detail above, the microchannel may be formed in a wide variety of channel geometries including semi-circular, rectangular, rhomboid, and the like, and the channels may be formed in a wide range of aspect ratios. The sample handling region of the microchannel from which the sample treatment components (214 through 220) are formed is typically rectangular; however, it may be laser ablated in any desired geometry. Furthermore, in any particular $\mu$-TAS, the sample handling regions of the microchannel may be formed in any combination of geometries including rectangular, square, triangular, and the like. In addition, while the $\mu$-TAS illustrated in FIG. 15 contains sample flow components with high aspect ratios (i.e., aspect ratios in which the depth of the microstructure is greater than the width) and sample treatment components with low aspect ratios (i.e., aspect ratios in which the width of the microstructure is greater than the depth), this is not intended to be limiting. For example, sample treatment components may have high aspect ratios, as in fourth sample treatment component 220.

As depicted in FIG. 15, $\mu$-TAS is a serial arrangement of alternating sample flow components 202 through 212 and sample treatment components 214 through 220. Optionally, detection means 232 through 240 are disposed along the sample flow components. The detection means may be formed in the cover plate, the substrate itself, or both the cover plate and the substrate, as described in greater detail above.

In addition, optional access ports (222 through 232) depicted in FIG. 15 are disposed along the sample flow components. The access ports allow the fluid communication of the sample flow component with, for example, external liquid reservoirs or mechanical valving necessary for the introduction or removal of samples, buffers and the like from the sample flow component as required to effect sample preparation by the $\mu$-TAS. External hardware may also be interfaced to the subject $\mu$-TAS to provide liquid handling capabilities, and a variety of means for applying a motive force along the length of the sample processing compartment may be associated with the $\mu$-TAS. Thus, access ports may be in divertable and switchable fluid communication with a valving manifold such that a valve in communication with an access port can be individually "actuated," i.e., opened to allow flow or closed to prevent flow through the access port.

In particular reference to FIG. 15, $\mu$-TAS 200 depicted therein contains first access port 222 by which sample may be introduced into first sample flow component 202 that is in fluid communication with first sample treatment component 214. The sample may be directly added to the sample flow component via first access port 222 without prior processing. Optionally, fist access port 222 may be interfaced with an external pre-column sample preparation device, e.g., a filtration device.

In one embodiment, sample treatment component 214 performs a filtration function and may be filled with a porous medium made of particles, sheets or membranes. In a preferred embodiment, the medium has an effective pore size of between 45 $\mu$m and 60 $\mu$m. Preferably, the medium is biocompatible and may be made from such materials as nylon, cellulose, polymethylmethacrylate, polyacrylamide, agarose, or the like. In an alternative embodiment, the filtration function may be performed by an in-line device prior to introduction of the sample into sample flow component 214.

In the particular embodiment depicted in FIG. 15, sample treatment component 214 is designed to serve a "capture" function. Thus, sample treatment component can be an affinity chromatography, ion exchange chromatography, a complexation reaction or any such quantal chromatographic technique (i.e., a chromatographic technique that could otherwise be performed in a batch mode rather than with a flowing sample stream). An affinity chromatography matrix may include a biological affiant, an antibody, a lectin, enzyme substrate or analog, enzyme inhibitor or analog, enzyme cofactor or analog, a capture oligonucleotide, or the like, depending on the nature of the sample. The ion exchange matrix may be an anionic or cationic ion exchange medium. Complexation reactions may include boronate reactions, dithiol reactions, metal-ion reactions, for example, with porphyrin or phenanthroline, or other reactions in which the sample is reversibly reacted with the chromatography matrix.

First and second access ports 222 and 224 are respectively disposed. upstream and downstream from first sample treatment component 214. When first access port 222 is used as an input port and second access port 224 is used as a withdrawal port, sample treatment component 214 can be isolated from downstream $\mu$-TAS sample handling regions. Thus, while a sample is loaded onto sample treatment component 214, extraneous materials which are flushed from the sample treatment component during analyte capture may be withdrawn and, in this manner, prevented from entering downstream $\mu$-TAS sample handling regions. Alternatively, second access port 224 may be used as an fluid input port to provide flow regulation, sample derivatization, or other like function when connected to a source of fluid which may be an external fluid source or an on-device fluid reservoir compartment (see FIG. 16).

Once a sample has been introduced into first sample flow component 214, sample flow may be effected by way of an external motive means which is interfaced with first access port 222. Alternatively, sample flow into sample treatment component 214 may be effected by activation of an on-device motive means, e.g., an on-device fluid reservoir compartment.

First detection means 234 may be in direct or indirect communication with second sample flow component 204 downstream from first sample treatment component 214. First detection means 234 can be used to monitor the presence of a sample in sample flow component 204 which is to be loaded onto second sample treatment component 216 or to monitor sample elution from first sample treatment component 214. In the latter case, it is preferred that first detection means 234 is placed in second sample flow component 204 upstream from second access port 224.

In the particular embodiment depicted in FIG. 15, second sample treatment component 216 serves to desalt or neutralize the analyte eluted from first sample treatment component 214. Thus, second sample treatment component 216 may be an electrophoretic desalting, pH neutralizing, size exclusion chromatography component, or the like.

As with first sample treatment component 214, second sample treatment component 216 is flanked by second and third access ports 224 and 226. First, second and third access ports 222, 224 and 226 may be used in any combination of inlet and outlet ports. Generally, once the sample has been eluted from first sample treatment component 214 and loaded onto second sample treatment component 216, second access port 224 serves as an inlet port and third access port 226 serves as an outlet port, thereby isolating second sample treatment component 216 from downstream $\mu$-TAS sample handling regions. In order to prevent backflow into first sample treatment component 214, first access port 222 can be closed.

As exemplified in FIG. 15, third sample treatment component 218 has been configured as an analyte focussing and pre-final sample processing compartment. As such, third sample treatment component 218 can be an isoelectric focusing component, an isotachophoretic sample stacking component, or the like. Again, third sample treatment component 218 is flanked by third and fourth access ports 226 and 228, which may be operated in a manner similar to that described for access port pairs 222/224 and 224/226 to isolate third sample treatment component 218 from downstream sample handling regions. Second and third detection means 236 and 238 may also be used as described above for first detection means 234.

Fourth sample treatment component 220 may include single or multiple functions selected from chromatographic, electrophoretic, or electro-chromatographic functions. Although only one sample treatment component 220 is shown in FIG. 15, multiple components of various dimensions can be laser ablated in continuum and specifically prepared as different sample processing functions in series. Examples of chromatographic functions which may be included in fourth sample treatment component 220 are reverse phase chromatography, hydrophobic interaction chromatography, affinity chromatography, size exclusion chromatography, ion exchange chromatography, chiral separation chromatography, and the like. For chromatographic functions, the stationary phase may be bonded or otherwise adhered to the surface of a particle or to the walls of the component. Examples of electrophoretic chromatography include open tubular electrophoresis, micellar electrokinetic capillary electrophoresis (see, Terabe et al. (1985) Anal. Chem. 57:834–831), capillary chiral electrophoresis, and the like. Open tubular electrophoresis includes bonded phase, dynamic deactivation using any of a variety of inorganic or organic reagents, isoelectric focussing, and the like. Micellar electrokinetic capillary chromatography may be done using surfactants such as sodium dodecyl sulfate, cetyl ammonium bromide, alkyl glucosides, alkyl maltosides, zwitterionic surfactants such as 3-[(3-cholamidopropyl)-dimethylammonio]-1-propane sulfonate ("CHAPS"), 3-[(3-cholamidopropyl)-dimethylammonio]-2-hydroxy-1-propane sulfonate ("CHAPSO"), or the like. Capillary chiral electrophoresis may be done using reagents such as cyclodextrins, crown ethers, bile salts, or the like.

Fourth detection means 240 can be situated in the sample flow component that is downstream from fourth sample treatment component 220. The detection means may be ablated into the substrate, cover plate, or both the substrate and the cover plate.

Optionally, as illustrated and described in detail in reference to FIGS. 7 and 8, fourth detection means 240 may be conduit means 72 comprising a laser-ablated aperture in the substrate 54 having an axis which is orthogonal to the first 56 and second 58 planar surfaces of the substrate, and communicating a distal end 74 of the sample processing compartment 60 with a first end 76 of a second microchannel 62 to form an extended sample processing compartment. As depicted in FIG. 9, this arrangement allows optical detection of sample analytes passing through the $\mu$-TAS to be carried out along an optical detection path length 86 corresponding to the major axis of the conduit means 72. In this manner, a wide variety of associated optical detection devices may be interfaced with a $\mu$-TAS constructed according to the invention, thereby allowing detection of analytes in samples passing through the conduit means 72 using UV/Vis, fluorescence, refractive index (RI), Raman and like spectrophotometric techniques.

In a further optional embodiment of the $\mu$-TAS, fifth access port 230 may serve one or more of a number of functions. As described above, fifth access port 230 may serve as an outlet port for fourth sample treatment component 220. It may optionally be attached to an external or on-device fluid reservoir compartment, thereby providing a means to regulate sample flow rates through the $\mu$-TAS or a means to introduce reagents into fifth sample flow component 210 which react with the sample to facilitate sample detection by fourth detection means 240.

Sixth access port 232 may serve one or more of a variety of functions as well including withdrawal of sample after final detection. Optionally, as with fifth access port 230, sixth access port 232 may be attached to a fluid reservoir compartment. In addition, sixth access port 232 may interface additional laser ablated microstructures for communicating a sample droplet to a post-column collection device (see FIGS. 17 and 18).

FIG. 16 illustrates a $\mu$-TAS 250 having a laser-ablated fluid reservoir compartment 252 as an integral "on-device" microstructure on the substrate. Fluid reservoir compartment 252 may be formed by laser ablation of a suitable microstructure in the substrate to provide a compartment in which buffers or other reagents may be held. Such reservoir compartment may be used to provide a makeup flow fluid, a flow regulation function or to provide a reagent for post-separation pre-detection analyte derivatization.

Figure 16B:
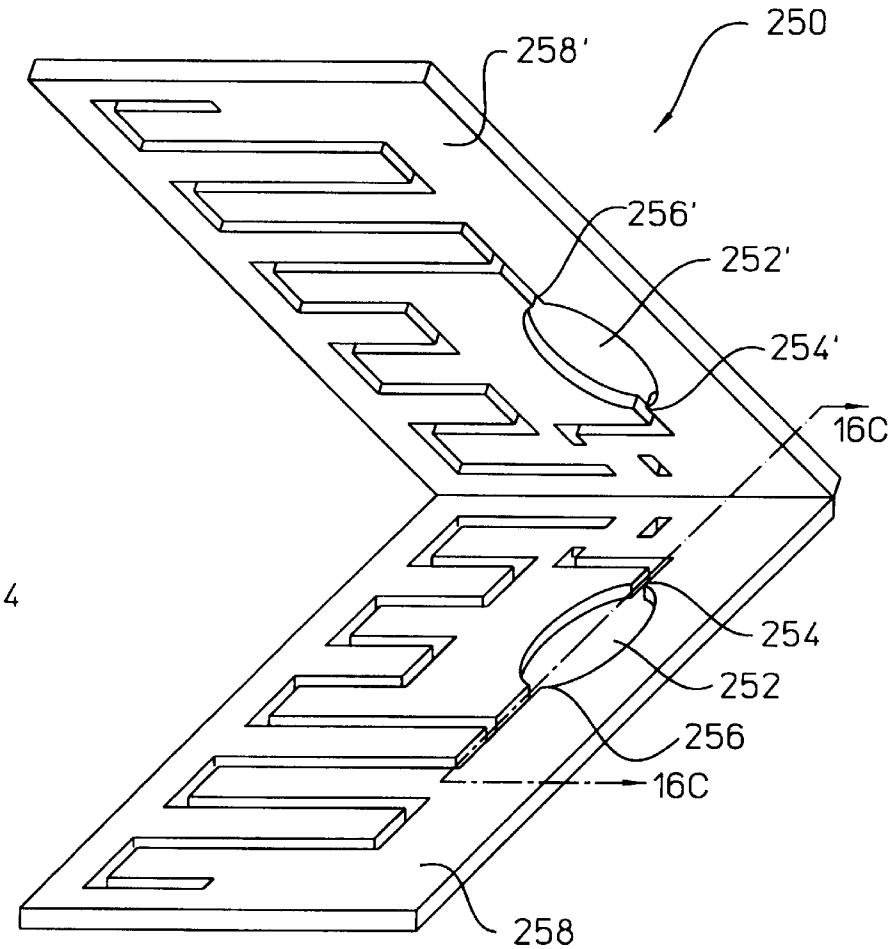
FIGS. 16A, 16B, and 16C are illustrations of a $\mu$-TAS having a laser-ablated reservoir compartment as an integral microstructure on the substrate.
Figure 16A:
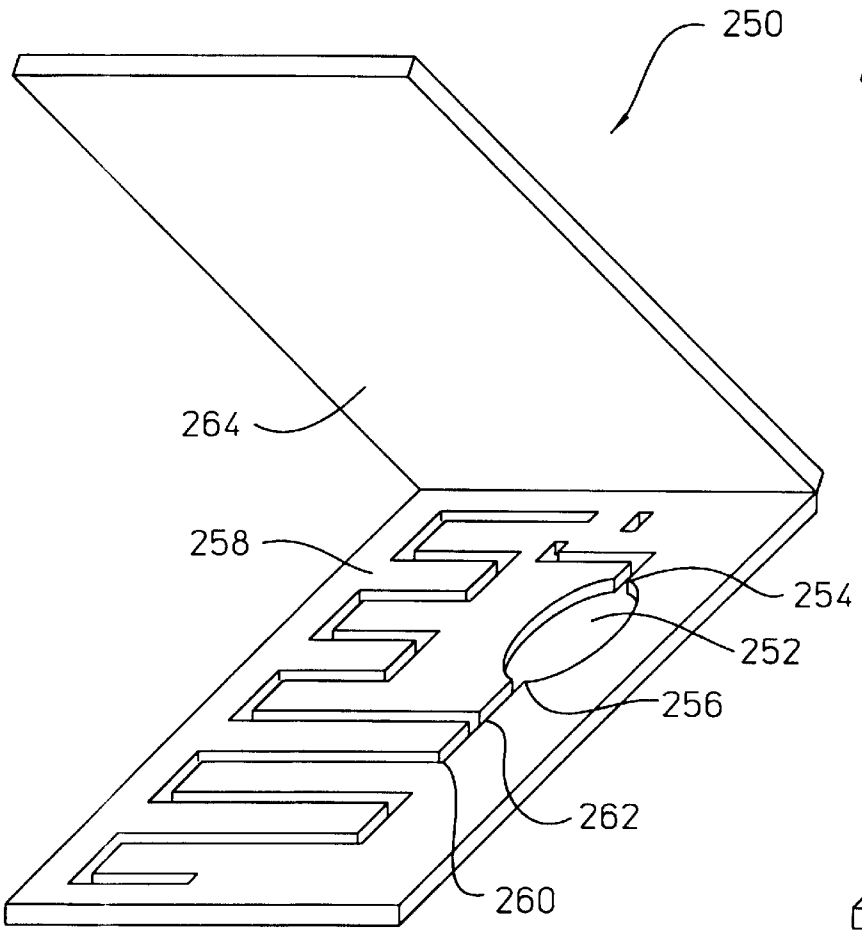

In one example depicted in FIG. 16A, reservoir microstructure 252 having inlet port 254 and outlet port 256 is laser ablated into planar substrate 258. The reservoir microstructure may be formed in any geometry and with any aspect ratio to provide a reservoir compartment having a desired volume. Outlet port 256 can be in fluid communication with sample processing compartment 260 by way of interconnecting microchannel 262. The inlet port is optionally divertably connected to an external source of fluid from which the reservoir compartment may be filled. The reservoir compartment 252, interconnecting reservoir flow component 262, and sample processing compartment 260 are respectively formed from the reservoir microstructure and the interconnecting microchannel in combination with cover plate 264.

In another example illustrated in FIG. 16B, fluid reservoir compartment 252 may be formed by laser ablating a reservoir microstructure 252 having an inlet port 254 and an outlet port 256 into first planar substrate 258 and mirror image structures 252', 254' and 256' in second planar substrate 258'. The reservoir compartment 252 is formed when the first and second substrates are aligned as described in detail above.

Buffers or reagents held in the fluid reservoir compartment may be delivered to sample processing compartment 260, to a sample flow component or to a sample treatment component reservoir compartment 252 via connecting microchannel 262. Fluid flow from the reservoir compartment to the sample processing compartment may occur via passive diffusion. Optionally, the fluid may be displaced from the reservoir compartment by an actuator means. A variety of micropumps and microvalves that will find utility as an actuator means according to the invention disclosed herein are well known in the art and have been described, for example, in Manz et al. (1993) Adv. Chromatogr. 33:1–66 and references cited therein.

Figure 16C:
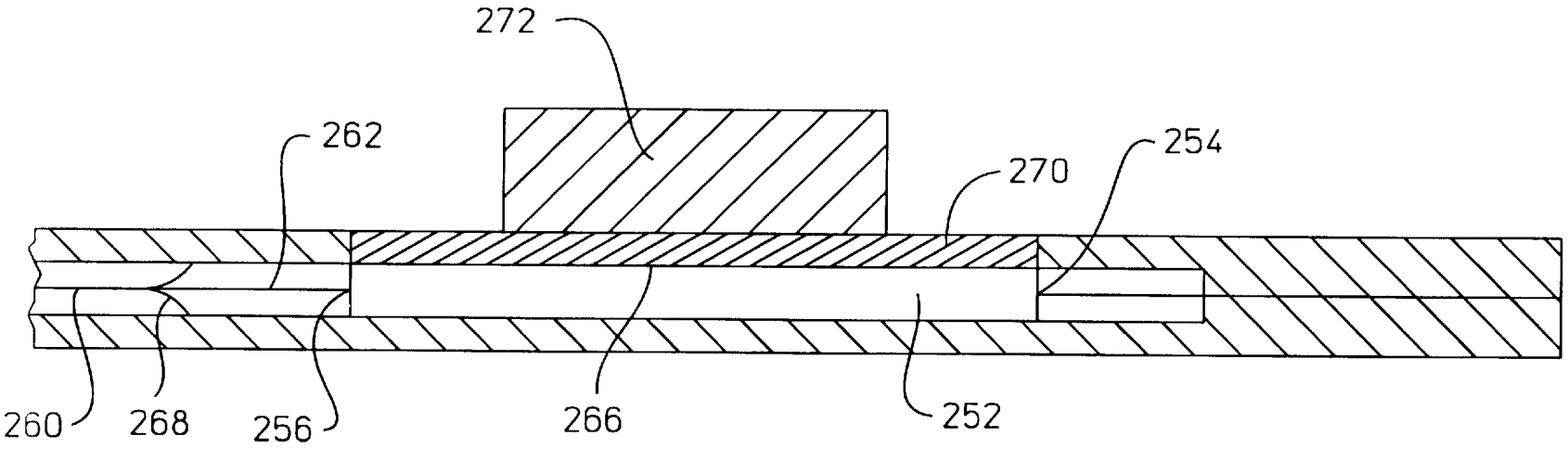

As illustrated in cross-section in FIG. 16C, the reservoir compartment 252 is optionally covered with thin membrane 266 to form a diaphragm-type pump; passive one-way microvalve 268 is optionally integrated into interconnecting microchannel 262 to prevent backflow of displaced fluid into the reservoir compartment. Optional gas- or liquid-filled cavity 270 is disposed above the membrane. Actuator means 272 can be employed to effect fluid displacement from reservoir compartment 252 by deflection of membrane 266.

Actuator means 272 may act to directly deflect membrane 266. Accordingly, the actuator means may be a piezoelectric, piston, solenoid or other type of membrane-deflecting device. Alternatively, the actuator means can be a heating means by which the temperature inside cavity 270 can be regulated. The heating means may be a resistance-type heating means or any type of suitable heating means known in the art. Upon actuation, the temperature of the heating means increases, thereby heating the contents of cavity 270 and increasing the volume thereof, producing a downward deflection of membrane 266, and displacing fluid from reservoir compartment 252, into interconnecting microchannel 262, past valve 268 and into sample processing compartment 260.

Alternatively, heating means 272 may be disposed in thermal contact with reservoir compartment 252 itself. In this configuration, as the heating means temperature increases, the volume of the fluid in the reservoir compartment increases and is thereby displaced from the reservoir compartment into the sample processing compartment.

Other examples of pumping mechanisms which may be incorporated into the $\mu$-TAS disclosed and claimed herein include those which operate on the principles of ultrasonic-induced transport (Moroney et al. (1991) Proc MEM S'91, p. 277) or electrohydrodynamic-induced transport (Richter et al. (1991) Proc MEM S'91 p. 271). In addition, chemical valves composed of electrically driven polyelectrolyte gels (Osada (1991) Adv. Materials 3:107; Osada et al. (1992) Nature 355:242) may be used.

Figure 17A:
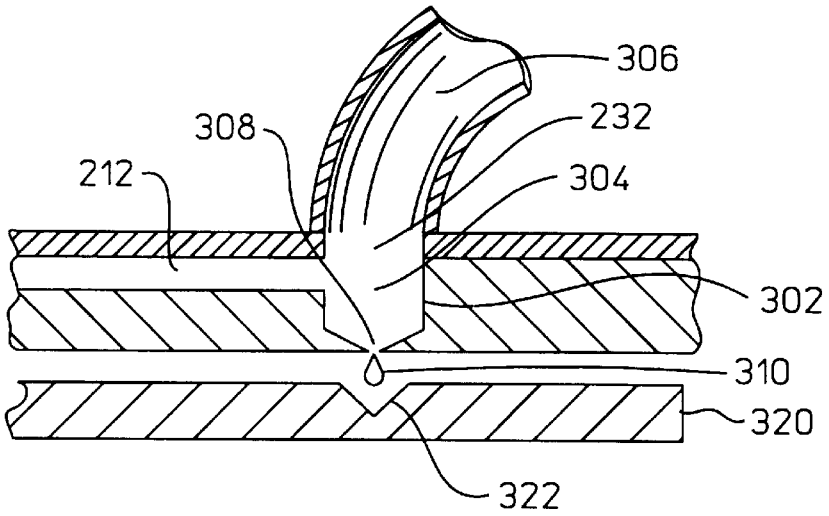
FIG. 17A is a cross-section of the $\mu$-TAS of FIG. 15 showing laser-ablated microstructures for communicating a sample droplet formed by a pressure pulse to a post-column sample collection device having a laser-ablated sample droplet receiving microwells.

Microstructures laser ablated in the substrate for communicating a sample droplet to a post-column sample collection device (320) are generally shown in FIG. 17, FIGS. 17A, 17B and 17C are cross-sections of a $\mu$-TAS illustrating means whereby sample droplets are generated and expelled from the $\mu$-TAS for post-column collection. Referring now to FIG. 17A, sixth sample flow component 212 and sixth access port 232 are in fluid communication with sample delivery means 302 comprising mixing chamber 304 in fluid communication and in axial alignment with sixth access port 232, fluid communication means 306 and an outlet nozzle 308. The fluid communication means 306 may be a conduit interfaced with an external source of fluid (FIG. 17A) or a microchannel (FIG. 17C) laser ablated in the substrate. As shown in FIG. 17A, fluid communication means 306 is in divertable fluid communication with an external reservoir of gas or liquid (not shown) and a means whereby a pulse of gas or liquid may be expelled from the external reservoir, thereby generating sample droplet 310. In FIG. 17A, post-column collection device 320 shown therein in cross-section may be a substrate in which sample droplet receiving microwell 322 has been laser ablated. As described with respect to other microstructures formed by laser ablation, microwell 322 may be of any geometry and any aspect ratio. Post-column collection device 320 is shown in greater detail in FIG. 18.

Figure 17B:
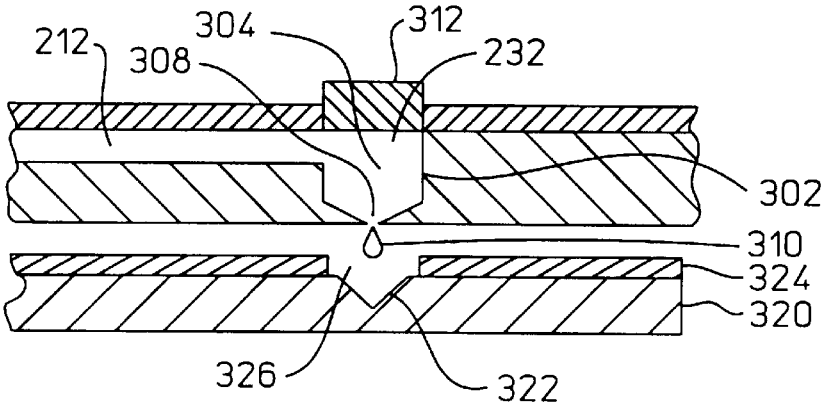
FIG. 17B is a cross-section of the $\mu$-TAS of FIG. 15 showing laser-ablated microstructures for communicating a sample droplet formed by a generating steam bubbles to a post-column sample collection device having laser-ablated sample droplet receiving microwells and a cover plate.

A further example of means for generating and expelling a sample droplet from a $\mu$-TAS is shown in cross-section in FIG. 17B. A heating means 312 can be situated in thermal contact with sample delivery means 302. As the temperature of heating means 312 increases, a steam bubble builds up in mixing chamber 304, thereby forming sample droplet 310. For further discussion of fluid delivery using this method see Allen et al. (1985) Hewlett-Packard J. May 1985:21–27. As in FIG. 17A, post-column collection device 320 shown in FIG. 17B in cross-section may be a substrate in which sample droplet receiving microwell 322 has been laser ablated. In addition, cover plate 324 may be movably interposed between the $\mu$-TAS and the post-column collection device 320. Cover plate 324 is a structure that has an opening 326 in axial alignment with nozzle 308 and receiving well 322 and is intended to provide protection of empty or filled wells from contamination or from evaporation of sample droplets previously collected.

Figure 17C:
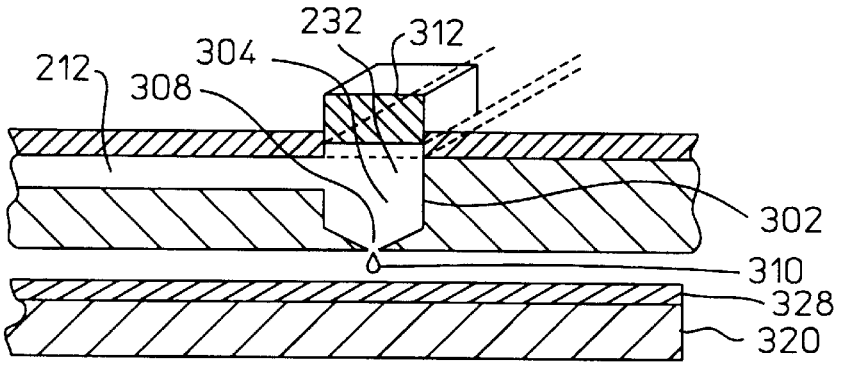
FIG. 17C is a cross-section of the $\mu$-TAS of FIG. 15 showing laser-ablated microstructures for communicating a sample droplet formed by a generating steam bubbles in a makeup fluid stream to a post-column sample collection device having a sample droplet receiving bibulous sheet means.

Yet another example of means for generating and expelling a sample droplet from a $\mu$-TAS is shown in cross-section in FIG. 17C. As illustrated in FIG. 17C, and in further reference to FIG. 16, fluid communication means 306 can be interconnecting microchannel 262 having a first end in fluid communication with sixth access port 232 and a second end in fluid communication with on-device fluid reservoir compartment 252. Alternatively, fluid communication means 306 may be a microchannel having a having a first end in fluid communication with sixth access port 232 and a second end terminating in an access port which is in fluid communication with an external fluid reservoir (not shown). Heating means 312 may be situated in thermal contact with fluid communication means 306. As described above, actuation of heating means 312 results in the increase in the temperature thereof, the build up of a steam bubble in mixing chamber 304, and the formation and expulsion of sample droplet 310. Fluid communication means 306 is optionally formed from a microchannel laser ablated in cover plate 264 or from mirror-image microchannels laser ablated in interior surfaces 258 and 258'. As in FIGS. 17A and 17B, post-column collection device 320 shown in FIG. 17C in cross-section may be a substrate which holds a bibulous sheet means 328 for solid-phase sample collection. Bibulous sheet means 328 for solid-phase sample collection may be filter paper, absorbent membranes, or the like. As described with respect to FIG. 17B, cover plate 324 may optionally be movably interposed between the $\mu$-TAS and the post-column collection device 320.

Figure 18A:
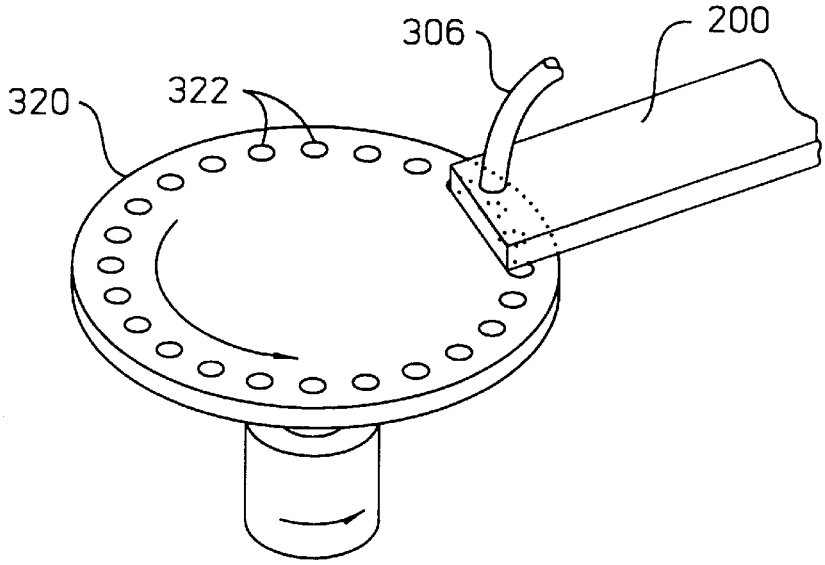
FIG. 18A is a pictorial representation of the $\mu$-TAS of FIG. 15 interfaced with a post-column collection device having sample droplet receiving wells.
Figure 18B:
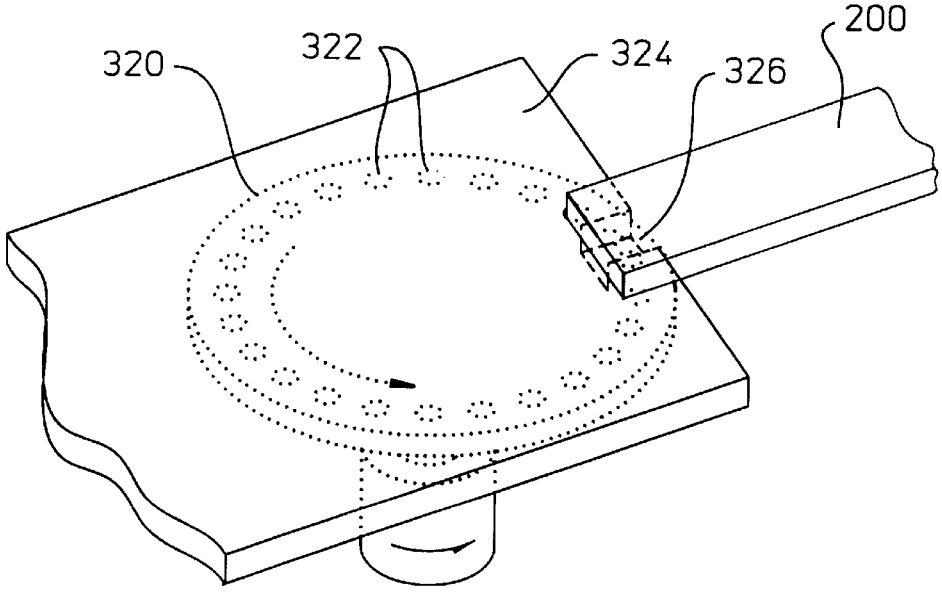
FIG. 18B is a pictorial representation of the $\mu$-TAS of FIG. 15 interfaced with a post-column collection device having sample droplet receiving wells and a cover plate.

As shown in FIG. 18, post-column collection device 320 comprising sample receiving means that may be sample receiving wells 322 or bibulous sheet means 328 can be positioned relative to nozzle means 308 to receive the sample droplet 310 from the nozzle means. The sample receiving means may be a microwell 322 laser ablated in a substrate for liquid phase sample collection or may be a bibulous sheet means 328 for solid-phase sample collection. The substrate for post-column collection device 320 is optionally a material other than silicon or silicon dioxide and microwells 322 are laser-ablated in the substrate. As shown in FIG. 18, the receiving means is optionally in rotatable alignment with the outlet nozzle such that multiple fractions may be connected. Alternatively, as shown in FIG. 18B, post-column collection device 320 includes protection means 324 with opening 326 in axial alignment with the outlet nozzle, wherein protection means 324 is interposed between $\mu$-TAS 200 and sample receiving wells 322. Although post-column collection device 320 is depicted as a disc in rotatable alignment with $\mu$-TAS 200, it will be recognized by one of skill in the art that the configuration of the collection device need not be so limited. Thus, post-column collection device 320 may be configured, for example, as a linear arrangement of sample receiving wells 322, or the like.

It is to be understood that while the invention has been described in conjunction with the preferred specific embodiments thereof, that the description above as well as the example which follows are intended to illustrate and not limit the scope of the invention. Other aspects, advantages and modifications within the scope of the invention will be apparent to those skilled in the art to which the invention pertains.

The following example is put forth so as to provide those of ordinary skill in the art with a complete disclosure and description of how to use the method of the invention, and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

Separation of Immunoglobulins from Serum

The serum sample used in this Example is composed of the following immunoglobulin analytes.

| | IgG | IgA | IgM |
|---|---|---|---|
| Concentration (mg/dl) | 1200 | 200 | 100 |
| $\mu$ | $\gamma$ | fast $\gamma$ to $\beta$ | fast $\gamma$ to $\beta$ |
| Mass (kDa) | 150 | 160 | 900 |

Examples of other serum constituents from which the immunoglobulin analytes will be extracted include albumin (4600 mg/dl), bilirubin (0.4 mg/dl), cholesterol (211 mg/dl), creatinine (1.1 mg/dl), glucose (108 mg/dl), calcium (9.8 mg/dl), phosphorous (4.0 mg/dl), nitrogen as urea (15 mg/dl) and uric acid (5.9 mg/dl).

A $\mu$-TAS device with exterior dimensions of approximately 20 mm×60 mm is fabricated using the laser ablation techniques described above in a polyimide material available under the trademark Kapton® from DuPont (Wilmington, Del.). Unless otherwise noted, the dimensions of the sample treatment components in millimeters are indicated below as width×length×depth.

First sample treatment component 214 is approximately 5×10×0.2. This provides component with a volume of 2.0 $\mu$l. The component is loaded with a matrix having a high surface area, for example, a microparticle or a membrane material, and having specificity for the analyte, in this case immunoglobulins G, A or M. The specificity of the analyte-matrix interaction is based on, for example, the hydrophobic nature of the analyte (e.g., reverse phase or hydrophobic interaction chromatography) or the ionic character of the analyte (e.g., ion exchange chromatography). On the other hand, the specificity may be based on the specific affinity of the matrix for the analyte. In either case, the function of the first sample treatment component is to "capture" the desired analyte and thereby provide a preconcentration function. First and second access ports 222 and 224 are laser ablated in the substrate and provide means by which fluids may be introduced into or withdrawn from first and second sample flow components 202 and 204 which flank first sample treatment component 214 and which are in fluid communication therewith. First and second ports 222 and 224 are in divertable communication with a valving manifold such that valves specifically associated with the indicated ports can be individually "actuated" to isolate this component during the "capture" step. In this manner, undesirable constituents in the samples are flushed to waste during sample loading and prior to elution of the analyte from the first sample treatment component.

For the purpose of the example, 5 $\mu$l of human serum, containing a total of about 150 femtomoles of IgG, 2.2 femtomoles of IgM and 25 femtomoles of IgA, is loaded onto first sample treatment component 214, which contains a membrane material containing protein A/G (Pierce) which binds to IgG, IgA and IgM. Sample loading may be done by injecting a bolus thereof or pumping the sample into the component through first access port 222. The sample is allowed to equilibrate with the protein in the first sample treatment component 214. The component is then flushed with a buffer solution to clear the chamber of other unbound solutes in the sample.

After the sample has equilibrated with the capture matrix in the first sample treatment component 214, valves associated with first and second access ports 222 and 224 are actuated, and a decoupling solution pumped through the component to elute the analyte from the matrix. A qualitative spectrophotometer optically coupled to first detection means 234 is monitored to determine when the analyte has been eluted from first sample treatment component 214 and has been loaded on the second sample treatment component 216.

Second sample treatment component 216 (3×30×0.2; 18 $\mu$l) is designed to serve a desalting function. There are several modes which may be used to desalt the analyte. For example, desalting can be accomplished using an electromotive separation based on the different mobilities of small and large solutes in a particular matrix. One alternative desalting method uses fluid pressure as a means for effecting mass transport, with size exclusion chromatography as the mode of separation. Further, it is possible that a mode combining both motive forces could be applied simultaneously, using an electrochromatography separation mode (see, e.g., Knox et al. (1987) Chromatographia 24:135; Knox et al. (1989) J. Liq. Chromatogr 12:2435; Knox et al. (1991) Chromatographia 32:317).

For the purpose of this example, second sample treatment component 216 contains an anti-convective media such as polyacrylamide, polymethylmethacrylate or agarose. Valves associated with second and third access ports 224 and 226 are actuated to isolate the second sample treatment component 216 during this step.

Third sample component 218 (3×40×0.2; 24 $\mu$l) serves an analyte band focusing function. After the capture and desalting steps, it is likely that band broadening will have occurred, and so a band focusing step is required. Analyte focusing can be done either by isoelectric focusing (IEF) mechanism in a gel matrix, chromatofocusing, or by isotachophoresis.

For the purpose of this example, third sample treatment component 218 contains a liquid ampholyte or an ampholyte in a gel matrix as described by Wehr et al (1990) Am. Biotechnol. Lab. 8:22 and Kilar et al. (1989) Electrophoresis 10:23–29.

Valves coupled to third and fourth access ports 226 and 228 are actuated in order to equilibrate the matrix in third sample treatment component 218 with the appropriate buffer. Valves communicating with second and fourth access ports 224 and 228 are then actuated to elute the analyte from second sample treatment component 216. Second detection means 326 is monitored to determine when all of the analyte has been loaded into third sample treatment component 218. Finally, the pH gradient is produced by actuating valves communicating with third and fourth access ports 226 and 228. A so-called polybuffer having an operating range of pH 7–4 or 9–6 (Sigma) is used. Separation of IgG from IgM and IgA occurs in this step.

Fourth sample treatment component 220 (50 $\mu$m×50 mm; 100 nl) effects the final separation of IgA from IgM. The separation is accomplished using capillary zone electrophoresis (CZE), in which the separation of IgA and IgM occurs based on the large difference between the charge/size ratio. As above, this component is loaded and isolated by actuation of valves in the manifold which communicate with fourth and fifth access ports 228 and 230 and sample loading is monitored via third detection means 238.

The last step of the exemplary determination of serum immunoglobulin analytes by the $\mu$-TAS occurs in fifth sample flow component 210 by monitoring fourth detection means 240. This is the detection on which analyte quatitation is based. Spectrophotometric detection would provide the quantitative data required. Fifth access port 230 is used as a means for introducing a reagent for post-column derivatization, e.g., dansylation or dabsylation, and detection. Femtomoles of immunoglobulins in nanoliters of final elution buffer yield micromolar to high nanomolar concentrations. Depending on the path length and mode of spectrophotometric detection, no reagent may be needed.

We claim:

1. A miniaturized total analysis system ($\mu$-TAS) comprising a miniaturized column device comprising:

(a) a substrate having first and second substantially planar opposing surfaces wherein said substrate is comprised of a material other than silicon or silicon dioxide, said substrate having a first microchannel laser-ablated in the first planar surface, wherein said first microchannel comprises more than one sample handling region;

(b) a cover plate arranged over the first planar surface, said cover plate in combination with the first microchannel forming a first sample processing compartment, wherein the sample handling regions define a sample flow component in fluid communication with a sample treatment component; and (c) at least one inlet port and at least one outlet port communicating with the first sample processing compartment, said inlet and outlet ports enabling the passage of fluid from an external source through the sample processing compartment.

2. The $\mu$-TAS of claim 1, wherein said first sample processing compartment comprises a serial arrangement of sample handling regions which define a serial arrangement of alternating sample flow components and sample treatment components.

3. The $\mu$-TAS of claim 2, further comprising detection means laser ablated in the substrate, wherein said detection means is in communication with the first sample processing compartment thereby enabling the detection of a sample passing through the sample processing compartment.

4. The $\mu$-TAS of claim 3, further comprising detection means laser ablated in the substrate, wherein said detection means is in communication with the sample flow component thereby enabling the detection of a sample passing through the sample processing compartment.

5. The $\mu$-TAS of claim 3, further comprising access ports in fluid communication of the sample flow component, thereby enabling the passage of fluid between an external source and the sample flow component.

6. The $\mu$-TAS of claim 2, further comprising access ports in fluid communication with the sample flow component, thereby enabling the passage of fluid between an external source and the sample flow component.

7. The $\mu$-TAS of claim 2, further comprising:

(a) a reservoir microstructure laser-ablated in the first planar surface, wherein the cover plate in combination with said microstructure define a reservoir compartment having an inlet means and an outlet means;

(b) a conducting microchannel laser-ablated in the first planar surface, wherein the cover plate in combination with said conducting microchannel defines a sample flow component having first and second ends respectively in fluid communication with the sample processing compartment and the reservoir compartment outlet means;

(c) an orifice in divertable fluid communication with the reservoir compartment inlet means, said orifice enabling the passage of fluid from an external source into the reservoir compartment; and (d) a motive means enabling the displacement of a fluid from the reservoir compartment through the sample flow component and into the first sample processing compartment.

8. The $\mu$-TAS of claim 7, further comprising:

(a) a sample delivery means in fluid communication with the first sample processing compartment outlet port, said sample delivery means comprising a mixing chamber in fluid communication and in axial alignment with a fluid communication means and an outlet nozzle;

(b) a fluid source in divertable fluid communication with the fluid communication means; and (c) a post-column collection device comprising a sample receiving means positioned relative to the outlet nozzle to receive eluent from the nozzle means.

9. The $\mu$-TAS of claim 2, further comprising:

(a) a sample delivery means in fluid communication with the first sample processing compartment outlet port, said sample delivery means comprising a mixing chamber in fluid communication and in axial alignment with a fluid communication means and an outlet nozzle;

(b) a fluid source in divertable fluid communication with the fluid communication means; and (c) a post-column collection device comprising a sample receiving means positioned relative to the outlet nozzle to receive eluent from the nozzle means.

10. The $\mu$-TAS of claim 2, further comprising:

(a) a second microchannel having an inlet port and an outlet port laser ablated in the second planar surface;

(b) a second cover plate disposed over the second planar surface, said cover plate in combination with the second microchannel defining a second sample processing compartment;

(c) conduit means for communicating the outlet port of the first sample processing compartment and the inlet port of the second sample processing compartment with each other thereby forming a single continuous sample processing compartment, said conduit means comprising a laser-ablated aperture in the substrate, said aperture having an axis which is orthogonal to the planar surfaces.

11. The $\mu$-TAS of claim 10, further comprising detection means comprising apertures laser-ablated respectively in the first and second cover plates and arranged in co-axial communication with the conduit means.

12. The $\mu$-TAS of claim 11, further comprising access ports in fluid communication of the sample flow component, thereby enabling the passage of fluid between an external source and the sample flow component.

13. The $\mu$-TAS of claim 10, further comprising access ports in fluid communication with the sample flow component, thereby enabling the passage of fluid between an external source and the sample flow component.

14. The $\mu$-TAS of claim 10, further comprising:

(a) a reservoir microstructure laser-ablated in the first planar surface, wherein the cover plate in combination with said microstructure define a reservoir compartment having an inlet means and an outlet means;

(b) a conducting microchannel laser-ablated in the first planar surface, wherein the cover plate in combination with said conducting microchannel defines a sample flow component having first and second ends respectively in fluid communication with the sample processing compartment and the reservoir compartment outlet means;

(c) an orifice in divertable fluid communication with the reservoir compartment inlet means, said orifice enabling the passage of fluid from an external source into the reservoir compartment; and (d) a motive means enabling the displacement of a fluid from the reservoir compartment through the sample flow component and into the first sample processing compartment.

15. The $\mu$-TAS of claim 14, further comprising:

(a) a sample delivery means in fluid communication with the first sample processing compartment outlet port, said sample delivery means comprising a mixing chamber in fluid communication and in axial alignment with a fluid communication means and an outlet nozzle;

(b) a fluid source in divertable fluid communication with the fluid communication means; and (c) a post-column collection device comprising a sample receiving means positioned relative to the outlet nozzle to receive eluent from the nozzle means.

16. The $\mu$-TAS of claim 10, further comprising:

(a) a sample delivery means in fluid communication with the first sample processing compartment outlet port, said sample delivery means comprising a mixing chamber in fluid communication and in axial alignment with a fluid communication means and an outlet nozzle;

(b) a fluid source in divertable fluid communication with the fluid communication means; and (c) a post-column collection device comprising a sample receiving means positioned relative to the outlet nozzle to receive eluent from the nozzle means.

17. A $\mu$-TAS device comprising:

(a) a support body formed from a substrate comprised of a material other than silicon or silicon dioxide, said support body having first and second component halves each having substantially planar interior surfaces;

(b) a first microchannel laser-ablated in the interior surface of the first support body half and a second microchannel laser-ablated in the interior surface of the second support body half, wherein said first and second microchannels are arranged so as to provide the mirror image of the other;

(c) a sample processing compartment formed by aligning the interior surfaces of the support body halves in facing abutment with each other whereby the microchannels define said sample processing compartment and wherein said sample processing compartment comprises sample handling regions which define a sample flow component in fluid communication with a sample treatment component; and (d) at least one inlet port and at least one outlet port communicating with the sample processing compartment, said ports enabling the passage of fluid from an external source through the sample processing compartment.

18. The $\mu$-TAS of claim 17, wherein said sample processing compartment comprises a serial arrangement of sample handling regions which define a serial arrangement of alternating sample flow components and sample treatment components.

19. The $\mu$-TAS of claim 18, further comprising detection means laser ablated in the substrate, wherein said detection means is in communication with the sample processing compartment thereby enabling the detection of a sample passing through the sample processing compartment.

20. The $\mu$-TAS of claim 19, further comprising detection means laser ablated in the substrate, wherein said detection means is in communication with the sample flow component thereby enabling the detection of a sample passing through the sample processing compartment.

21. The $\mu$-TAS of claim 19, further comprising access ports in fluid communication of the sample flow component, thereby enabling the passage of fluid between an external source and the sample flow component.

22. The $\mu$-TAS of claim 18, further comprising access ports in fluid communication with the sample flow component, thereby enabling the passage of fluid between an external source and the sample flow component.

23. The $\mu$-TAS of claim 18, further comprising:

(a) a reservoir microstructure laser-ablated in the first planar surface, wherein the cover plate in combination with said microstructure define a reservoir compartment having an inlet means and an outlet means;

(b) a conducting microchannel laser-ablated in the first planar surface, wherein the cover plate in combination with said conducting microchannel defines a sample flow component having first and second ends respectively in fluid communication with the sample processing compartment and the reservoir compartment outlet means;

(c) an orifice in divertable fluid communication with the reservoir compartment inlet means, said orifice enabling the passage of fluid from an external source into the reservoir compartment; and (d) a motive means enabling the displacement of a fluid from the reservoir compartment through the sample flow component and into the sample processing compartment.

24. The $\mu$-TAS of claim 23, further comprising:

(a) a sample delivery means in fluid communication with the sample processing compartment outlet port, said sample delivery means comprising a mixing chamber in fluid communication and in axial alignment with a fluid communication means and an outlet nozzle;

(b) a fluid source in divertable fluid communication with the fluid communication means; and (c) a post-column collection device comprising a sample receiving means positioned relative to the outlet nozzle to receive eluent from the nozzle means.

25. The $\mu$-TAS of claim 18, further comprising:

(a) a sample delivery means in fluid communication with the first sample processing compartment outlet port, said sample delivery means comprising a mixing chamber in fluid communication and in axial alignment with a fluid communication means and an outlet nozzle;

(b) a fluid source in divertable fluid communication with the fluid communication means; and (c) a post-column collection device comprising a sample receiving means positioned relative to the outlet nozzle to receive eluent from the nozzle means.

*26. The $\mu$-TAS device of claim 17, wherein the support body further comprises a fold means separating said first and second component halves.*

*27. The $\mu$-TAS device of claim 18, wherein the support body further comprises a fold means separating said first and second component halves.*

*28. The $\mu$-TAS device of claim 23, wherein the support body further comprises a fold means separating said first and second component halves.*

*29. The $\mu$-TAS device of claim 25, wherein the support body further comprises a fold means separating said first and second component halves.*

*30. The $\mu$-TAS device of claim 26, wherein said first and second component halves further comprise micro-alignment means.*

*31. The μ-TAS device of claim 27, wherein said first and second component halves further comprise micro-alignment means.*

*32. The μ-TAS device of claim 28, wherein said first and second component halves further comprise micro-alignment means.*

*33. The μ-TAS device of claim 29, wherein said first and second component halves further comprise micro-alignment means.*

*34. The μ-TAS device of claim 30, wherein said micro-alignment means comprises a plurality of holes laser-ablated in said component halves, wherein the holes are arranged such that alignment of corresponding holes in said first and second component halves enables the precise alignment of said first and second microchannels to form said sample processing compartment.*

*35. The μ-TAS device of claim 31, wherein said micro-alignment means comprises a plurality of holes laser-ablated in said component halves, wherein the holes are arranged such that alignment of corresponding holes in said first and second component halves enables the precise alignment of said first and second microchannels to form said sample processing compartment.*

*36. The μ-TAS device of claim 32, wherein said micro-alignment means comprises a plurality of holes laser-ablated in said component halves, wherein the holes are arranged such that alignment of corresponding holes in said first and second component halves enables the precise alignment of said first and second microchannels to form said sample processing compartment.*

*37. The μ-TAS device of claim 33, wherein said micro-alignment means comprises a plurality of holes laser-ablated in said component halves, wherein the holes are arranged such that alignment of corresponding holes in said first and second component halves enables the precise alignment of said first and second microchannels to form said sample processing compartment.*

*38. The μ-TAS device of claim 30, wherein said micro-alignment means comprises corresponding structures formed in said component halves, said structures comprising a plurality of depressions arranged on one of said component halves and a plurality of projections arranged on the other of said component halves, said projections configured to mate with said depressions such that alignment of the corresponding structures enables the precise alignment of said first and second microchannels to form said sample processing compartment.*

*39. The μ-TAS device of claim 31, wherein said micro-alignment means comprises corresponding structures formed in said component halves, said structures comprising a plurality of depressions arranged on one of said component halves and a plurality of projections arranged on the other of said component halves, said projections configured to mate with said depressions such that alignment of the corresponding structures enables the precise alignment of said first and second microchannels to form said sample processing compartment.*

*40. The μ-TAS device of claim 32, wherein said micro-alignment means comprises corresponding structures formed in said component halves, said structures comprising a plurality of depressions arranged on one of said component halves and a plurality of projections arranged on the other of said component halves, said projections configured to mate with said depressions such that alignment of the corresponding structures enables the precise alignment of said first and second microchannels to form said sample processing compartment.*

*41. The μ-TAS device of claim 33, wherein said micro-alignment means comprises corresponding structures formed in said component halves, said structures comprising a plurality of depressions arranged on one of said component halves and a plurality of projections arranged on the other of said component halves, said projections configured to mate with said depressions such that alignment of the corresponding structures enables the precise alignment of said first and second microchannels to form said sample processing compartment.*

*42. The μ-TAS device comprising:*

*(a) a substrate formed from a substrate comprised of a material other than silicon or silicon dioxide, said substrate having a column portion and first and second cover plate portions,*

*said column portion having first and second substantially planar opposing surfaces,*

*said first and second cover plate portions each having at least one substantially planar surface,*

*said first cover plate portion separated from said column portion by at least one fold means such that said planar surface of said first cover plate portion can be folded to overlie said first planar surface of said column portion,*

*said second cover plate portion separated from said column portion by at least one fold means such that said planar surface of said second cover plate portion can be folded to overlie said second planar surface of said column portion;*

*(b) a first microchannel laser-ablated in said first surface of said column portion and a second microchannel laser-ablated in said second surface of said column portion;*

*(c) a conduit means laser ablated through said column portion communicating with a distal portion of said first microchannel and a first portion of said second microchannel;*

*(d) a separation compartment formed by aligning said planar surface of said first cover plate portion with said first surface of said column portion by folding said first fold means, and by further aligning said planar surface of said second cover plate portion with said second surface of said column portion by folding said second fold means; and*

*(e) a first aperture laser ablated in said first cover plate portion allowing fluid communication with said first microchannel and a second aperture laser ablated in said second cover plate portion allowing fluid communication with said second microchannel.*

* * * * *